United States Patent
Singhatat et al.

(10) Patent No.: US 10,022,122 B2
(45) Date of Patent: Jul. 17, 2018

(54) SUTURE BASED TISSUE REPAIR

(75) Inventors: Wamis Singhatat, Malvern, PA (US); James Talbot, Lititz, PA (US); Michael Keane, Downingtown, PA (US); Brian Schmidt, Perkasie, PA (US); Mark Reichen, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 1041 days.

(21) Appl. No.: 12/995,758

(22) PCT Filed: Jun. 8, 2009

(86) PCT No.: PCT/US2009/046624
§ 371 (c)(1),
(2), (4) Date: Dec. 2, 2010

(87) PCT Pub. No.: WO2009/149455
PCT Pub. Date: Dec. 10, 2009

(65) Prior Publication Data
US 2011/0077667 A1 Mar. 31, 2011

Related U.S. Application Data

(60) Provisional application No. 61/059,584, filed on Jun. 6, 2008.

(51) Int. Cl.
*A61B 17/04* (2006.01)
*A61B 17/00* (2006.01)
*A61B 17/08* (2006.01)

(52) U.S. Cl.
CPC ...... *A61B 17/0487* (2013.01); *A61B 17/0401* (2013.01); *A61B 17/0469* (2013.01);
(Continued)

(58) Field of Classification Search
CPC . A61B 17/0401; A61B 17/0466; A61B 17/82; A61B 17/823; A61B 17/0487;
(Continued)

(56) References Cited

U.S. PATENT DOCUMENTS 3,002,780 A * 10/1961 Eggeman .................. B66C 1/14
24/129 R
3,409,014 A * 11/1968 Shannon ....................... 606/148
(Continued)

FOREIGN PATENT DOCUMENTS

CN 102088915 6/2011
EP 1 568 326 8/2005
(Continued)

OTHER PUBLICATIONS

Machine-generated translation of FR 2717065 from Espacenet, accessed Aug. 9, 2016; pp. 1-7.*
(Continued)

*Primary Examiner* — Christopher L Templeton
(74) *Attorney, Agent, or Firm* — Baker & Hostetler LLP

(57) ABSTRACT

The present invention provides an apparatus for suture-based tissue repair, preferably for the annulus of a spinal disc, that includes a suture loop preferably pre-tied with a sliding knot, a clasp-type component that captures the ends of the suture loop, and an optional plug member that fills the tissue defect. Also disclosed is a method that places the suture loop in a full-thickness stitch encircling the tissue defect, secures the ends of the suture loop to the clasp, and cinches the suture loop to approximate the tissue without the need to tie knots. Also disclosed is a suture passer that enables a suture strand or loop to be passed through the tissue wall, captured, and retrieved. The suture passer may optionally incorporate a clasp in such an arrangement that
(Continued)

enables a suture loop passed through the tissue wall to be captured directly by the clasp.

19 Claims, 20 Drawing Sheets

(52) U.S. Cl.
CPC ....... *A61B 17/0057* (2013.01); *A61B 17/0466* (2013.01); *A61B 2017/00637* (2013.01); *A61B 2017/00663* (2013.01); *A61B 2017/0409* (2013.01); *A61B 2017/0475* (2013.01); *A61B 2017/081* (2013.01)

(58) Field of Classification Search
CPC ..... A61B 17/081; A61B 17/08; A61B 17/132; A61B 17/1322; A61B 17/1327; A61B 17/12; A61B 17/128; A61B 2017/0406; A61B 2017/0404; A61B 2017/0409; A61B 2017/0414; A61B 2017/0459; A61B 2017/0464; A61B 2017/088; A61B 2017/0475; A61B 2017/081; A61B 17/0057; A61B 2017/0477; A61B 2017/00663; A61B 2017/1103; Y10T 24/1408; A61F 2/0811; A61F 2002/0817; A61F 2002/0852; A61F 2002/0882
USPC ....... 606/139, 144, 148, 216, 215, 217, 232, 606/151; 623/13.13, 13.14, 17.11–17.16; 24/129 R
See application file for complete search history.

(56) References Cited

U.S. PATENT DOCUMENTS

| | | | | |
|---|---|---|---|---|
| 3,880,166 | A * | 4/1975 | Fogarty | 606/158 |
| 4,355,444 | A * | 10/1982 | Haney | 24/129 B |
| 4,823,794 | A * | 4/1989 | Pierce | 606/232 |
| 5,129,912 | A * | 7/1992 | Noda et al. | 606/139 |
| 5,219,359 | A * | 6/1993 | McQuilkin et al. | 606/232 |
| 5,232,193 | A * | 8/1993 | Skakoon | 251/4 |
| 5,284,485 | A * | 2/1994 | Kammerer et al. | 606/148 |
| 5,300,078 | A * | 4/1994 | Buelna | 606/113 |
| 5,312,423 | A * | 5/1994 | Rosenbluth et al. | 606/148 |
| 5,336,231 | A * | 8/1994 | Adair | 606/148 |
| 5,527,341 | A * | 6/1996 | Gogolewski et al. | 606/232 |
| 5,709,708 | A * | 1/1998 | Thal | 606/232 |
| 5,782,866 | A * | 7/1998 | Wenstrom, Jr. | A61B 17/0401 606/232 |
| 6,063,106 | A * | 5/2000 | Gibson | 606/232 |
| 6,106,545 | A * | 8/2000 | Egan | 606/232 |
| 6,149,653 | A * | 11/2000 | Deslauriers | 606/232 |
| 6,193,754 | B1 * | 2/2001 | Seedhom | 623/13.11 |
| 6,514,274 | B1 * | 2/2003 | Boucher | A61B 17/0401 606/232 |
| 6,767,037 | B2 * | 7/2004 | Wenstrom, Jr. | 289/1.2 |
| 6,821,285 | B2 | 11/2004 | Laufer et al. | |
| 7,887,551 | B2 * | 2/2011 | Bojarski et al. | 606/139 |
| 8,454,635 | B2 * | 6/2013 | Paolitto et al. | 606/158 |
| 2001/0051816 | A1 * | 12/2001 | Enzerink et al. | 606/232 |
| 2002/0019649 | A1 * | 2/2002 | Sikora et al. | 606/232 |
| 2003/0130694 | A1 * | 7/2003 | Bojarski | A61B 17/0401 606/228 |
| 2004/0015171 | A1 * | 1/2004 | Bojarski et al. | 606/72 |
| 2004/0116943 | A1 * | 6/2004 | Brandt et al. | 606/144 |
| 2004/0133238 | A1 * | 7/2004 | Cerier | 606/232 |
| 2004/0147958 | A1 * | 7/2004 | Lam et al. | 606/232 |
| 2004/0153074 | A1 * | 8/2004 | Bojarski | A61B 17/0401 606/232 |
| 2004/0225325 | A1 * | 11/2004 | Bonutti | 606/232 |
| 2005/0187577 | A1 * | 8/2005 | Selvitelli et al. | 606/232 |
| 2005/0251205 | A1 * | 11/2005 | Ewers et al. | 606/232 |
| 2005/0288711 | A1 * | 12/2005 | Fallin et al. | 606/232 |
| 2006/0142784 | A1 | 6/2006 | Kontos | |
| 2006/0287731 | A1 | 12/2006 | Cauthen et al. | |
| 2007/0027476 | A1 * | 2/2007 | Harris et al. | 606/232 |
| 2007/0032792 | A1 * | 2/2007 | Collin et al. | 606/72 |
| 2007/0100348 | A1 | 5/2007 | Cauthen, III et al. | |
| 2007/0203506 | A1 * | 8/2007 | Sibbitt, Jr. | A61B 17/0057 606/139 |

FOREIGN PATENT DOCUMENTS

| | | |
|---|---|---|
| EP | 1 908 408 | 4/2008 |
| FR | 2 717 065 | 9/1995 |
| JP | 2003-502098 | 1/2003 |
| JP | 2003-284722 | 10/2003 |
| JP | 2007-501101 | 1/2007 |
| JP | 2007-090062 | 4/2007 |
| JP | 2011-522632 | 8/2011 |
| WO | WO 00/78227 | 12/2000 |
| WO | WO 2008/079826 | 7/2008 |
| WO | WO 2009/149455 | 12/2009 |

OTHER PUBLICATIONS

International Patent Application No. PCT/US2009/046624: International Search Report dated Sep. 17, 2009, 5 pages.

* cited by examiner

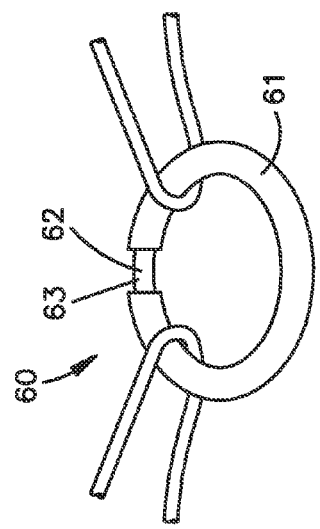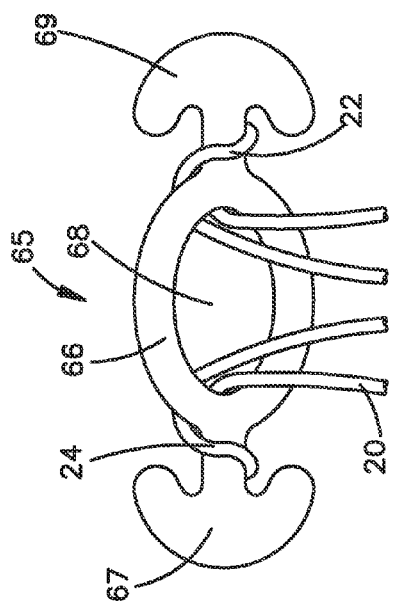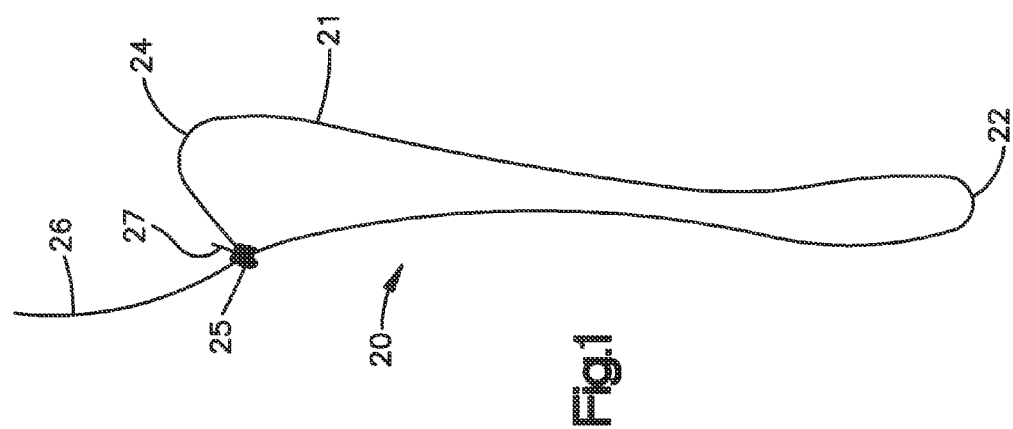

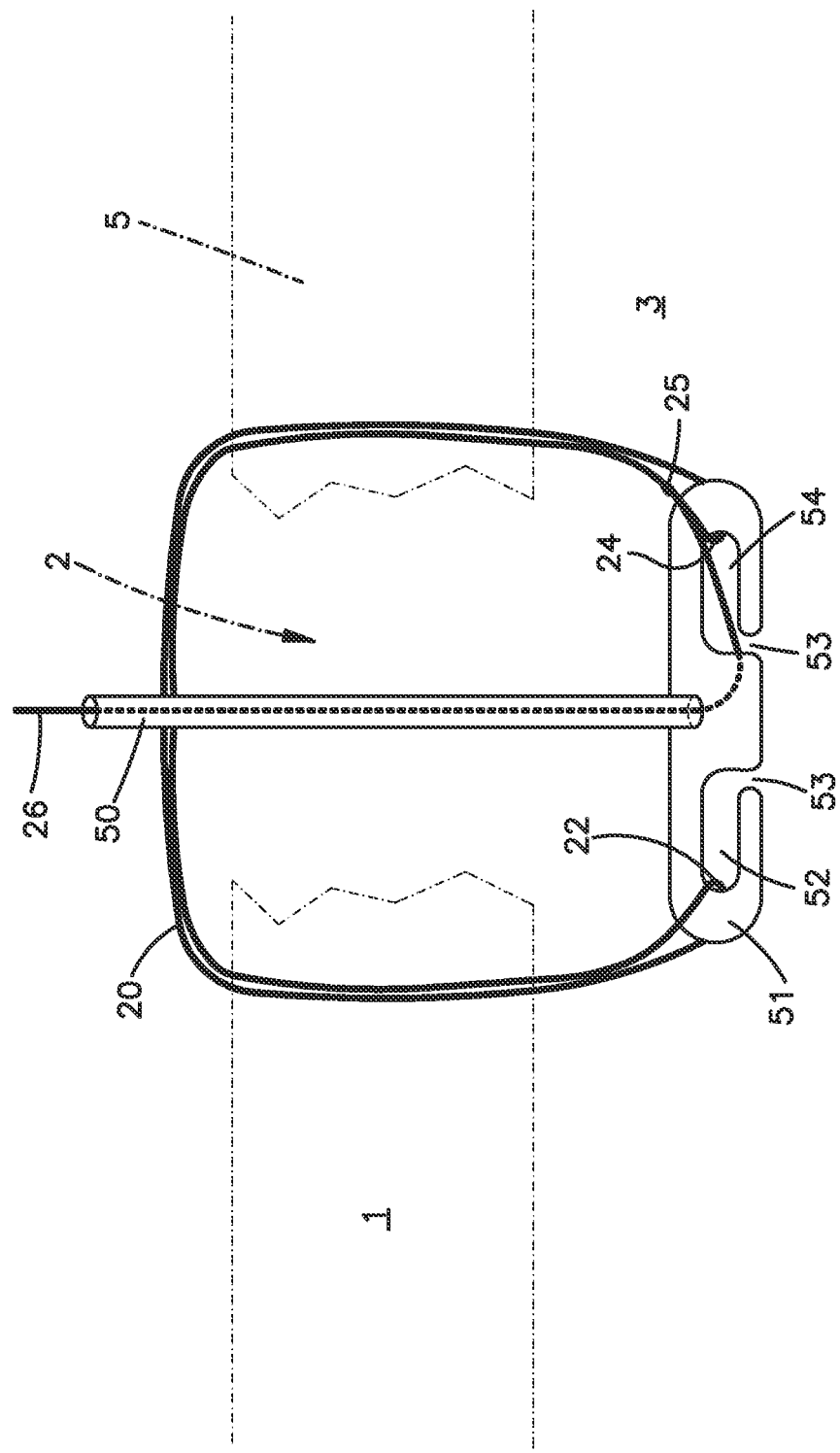

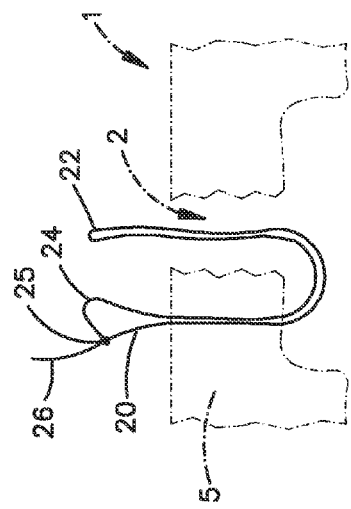
Fig.5B
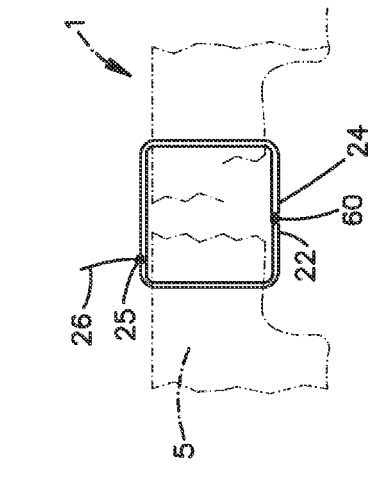
Fig.5E
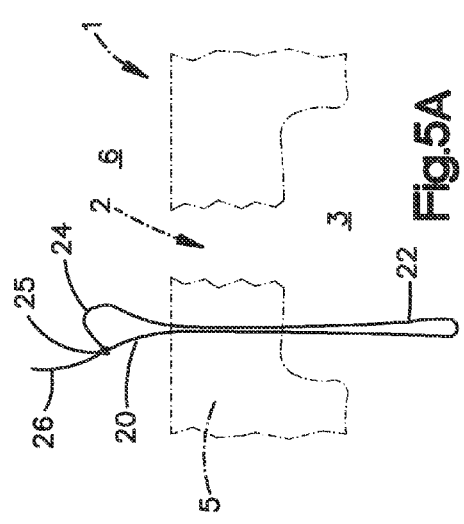
Fig.5A
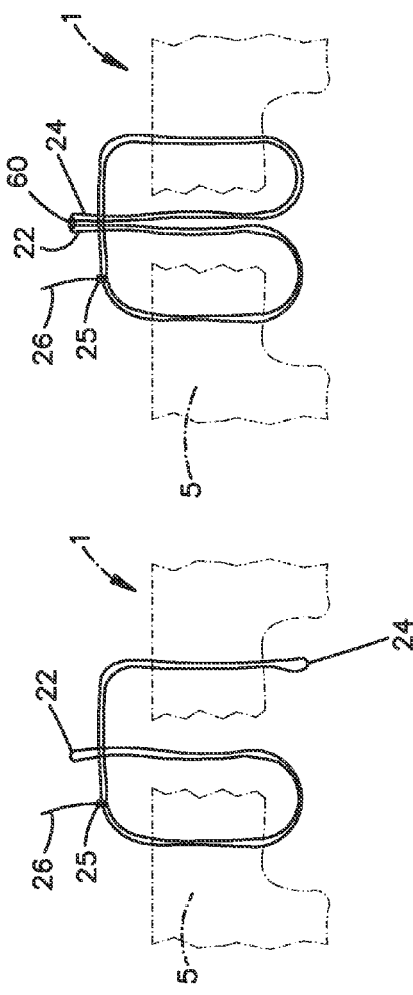
Fig.5D
Fig.5C

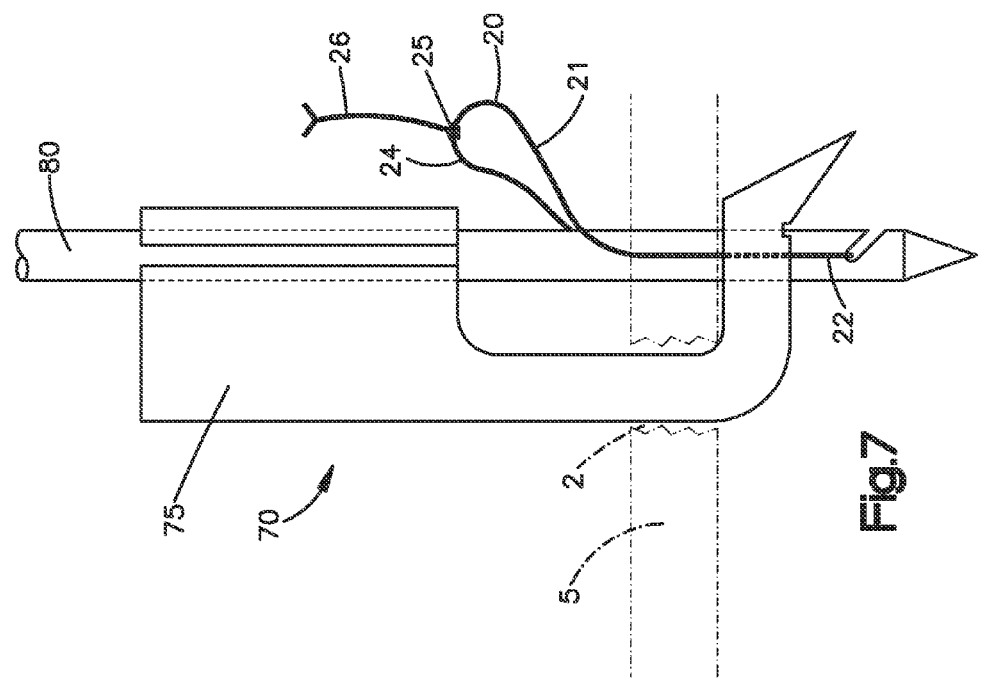
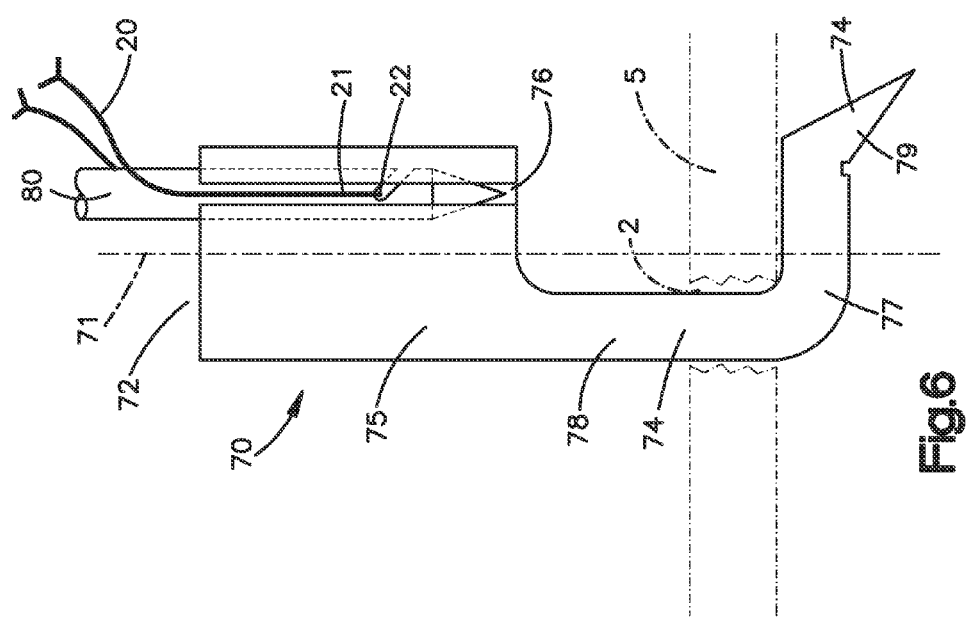

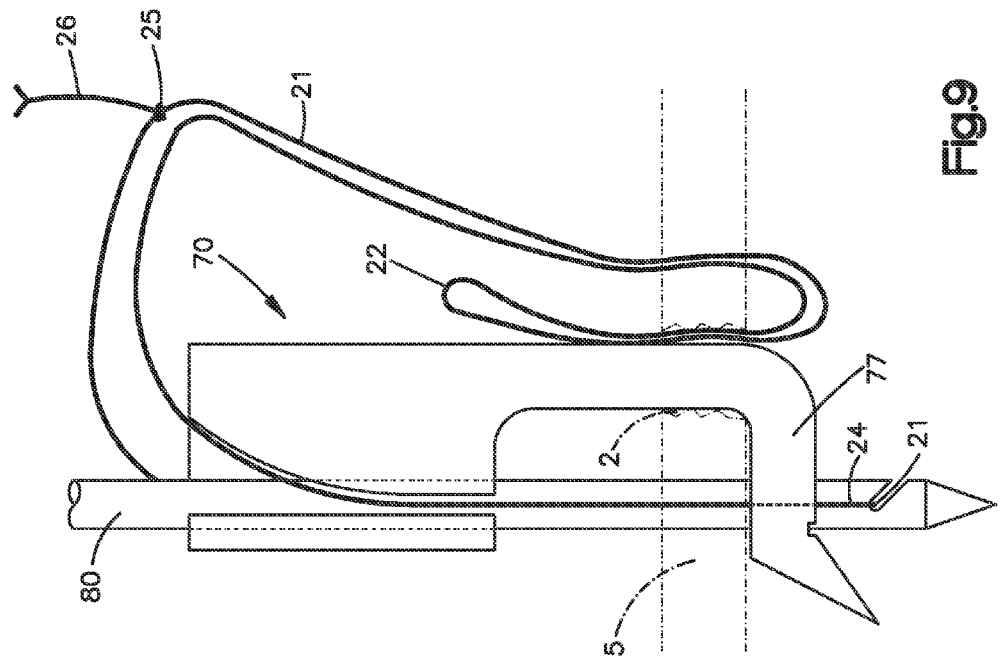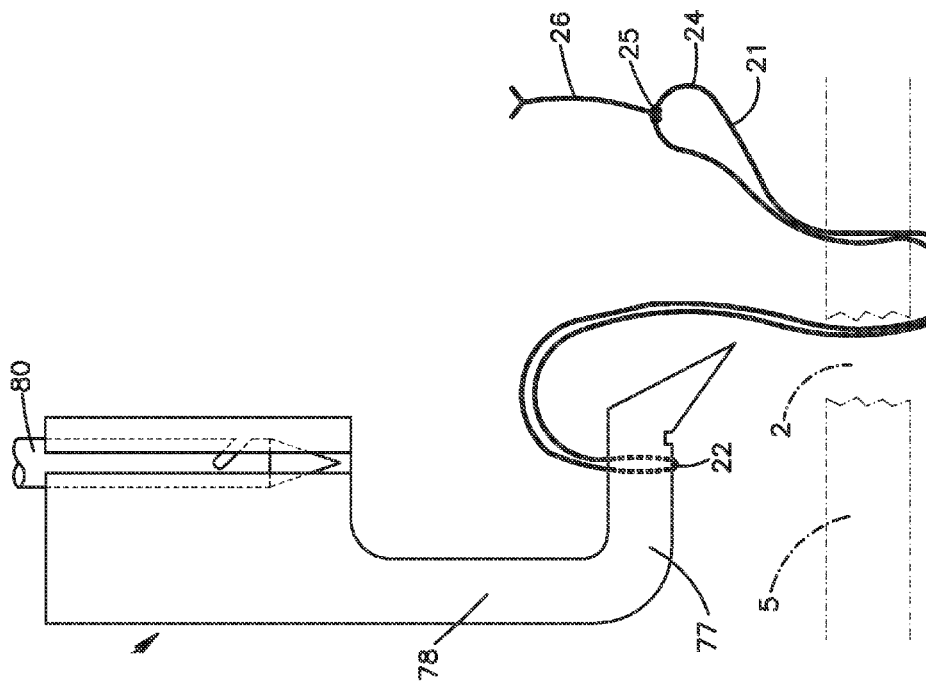

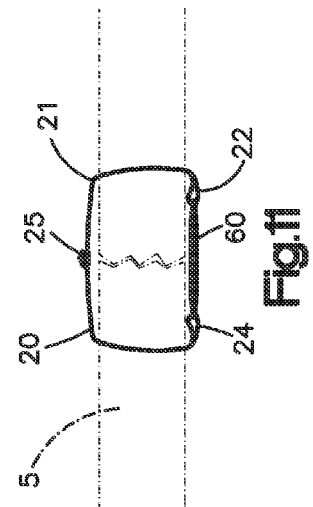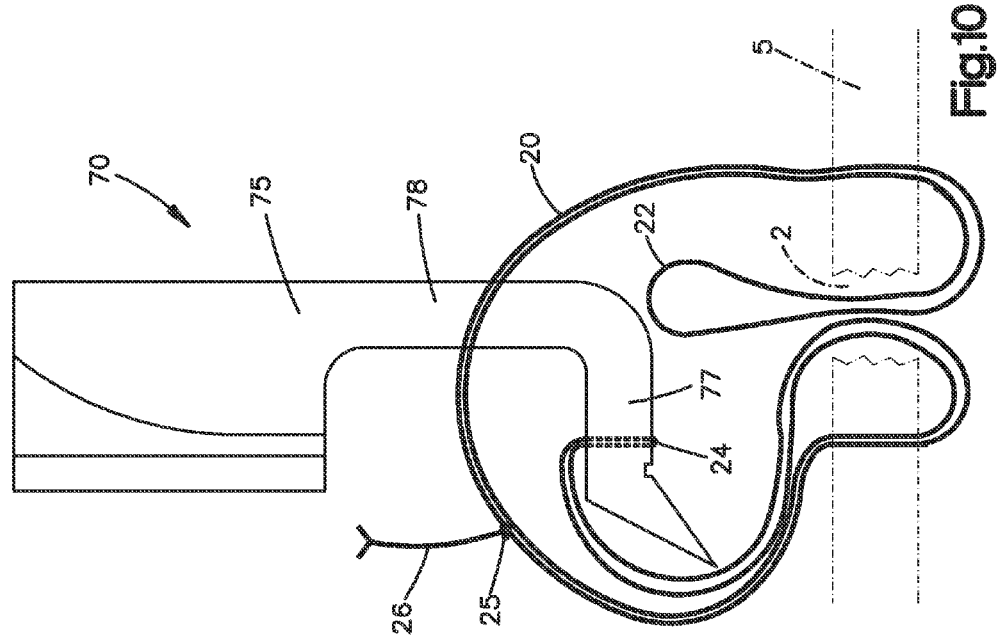

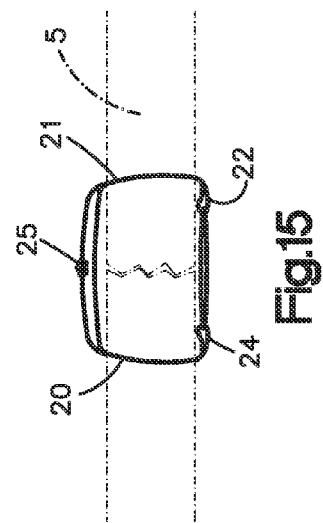
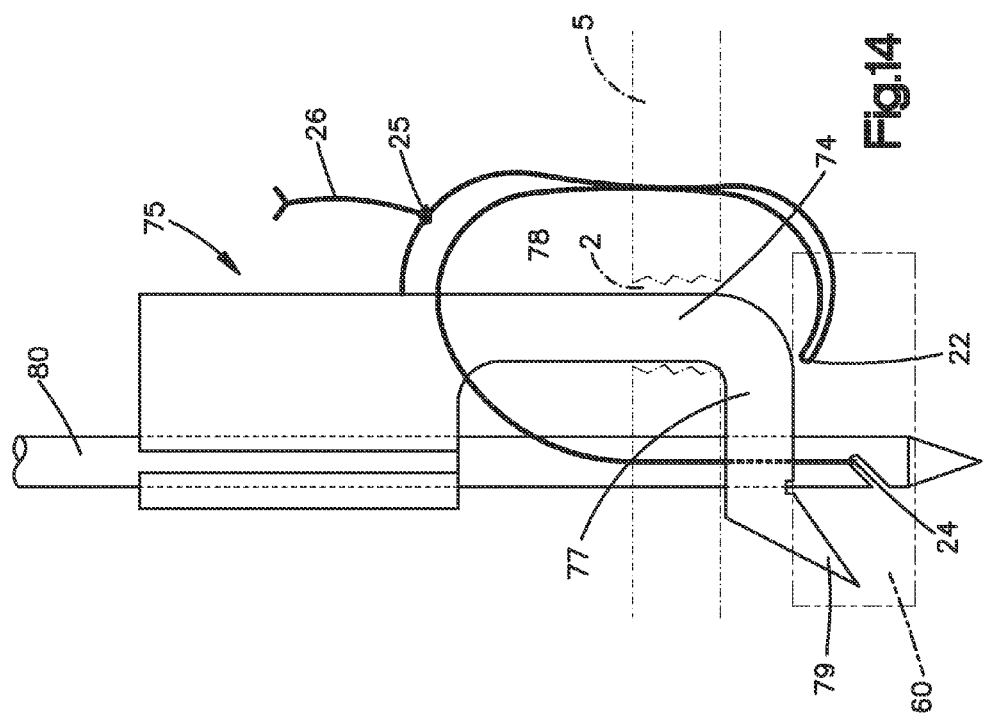

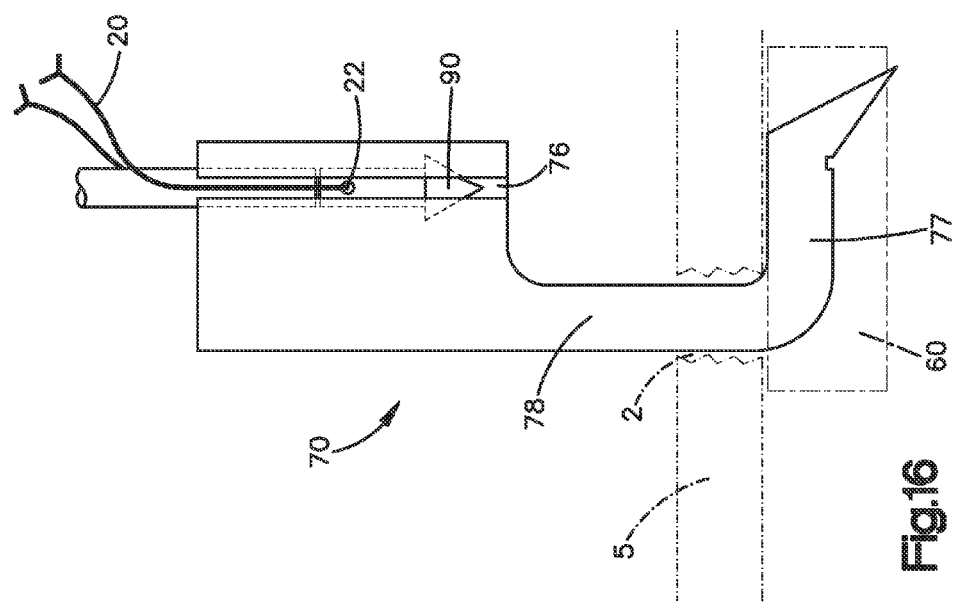

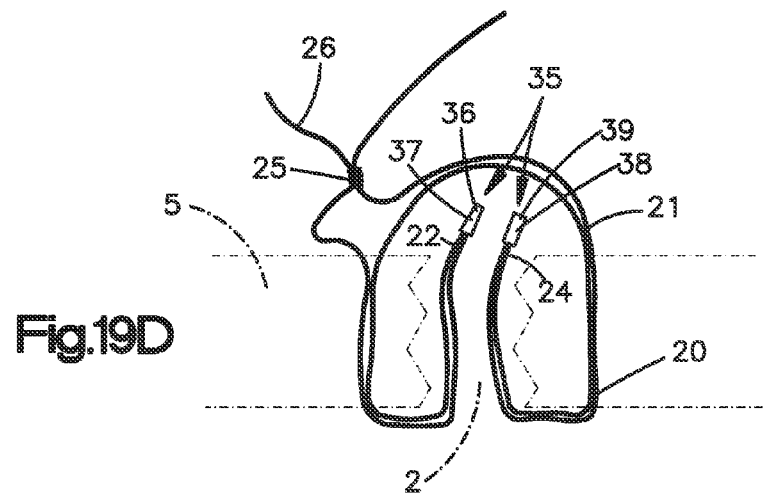
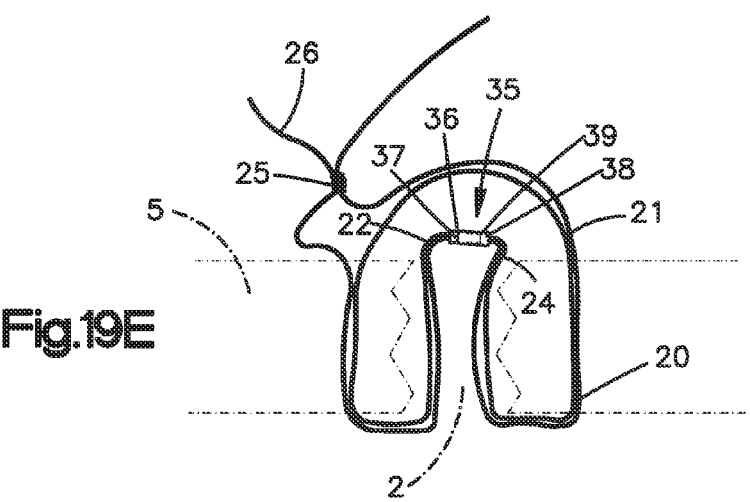
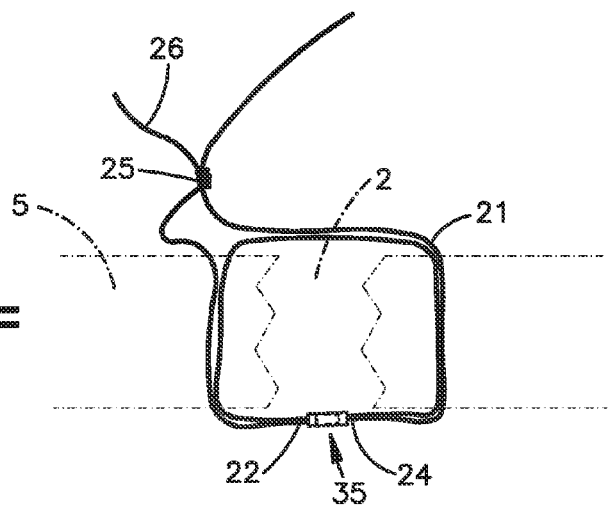

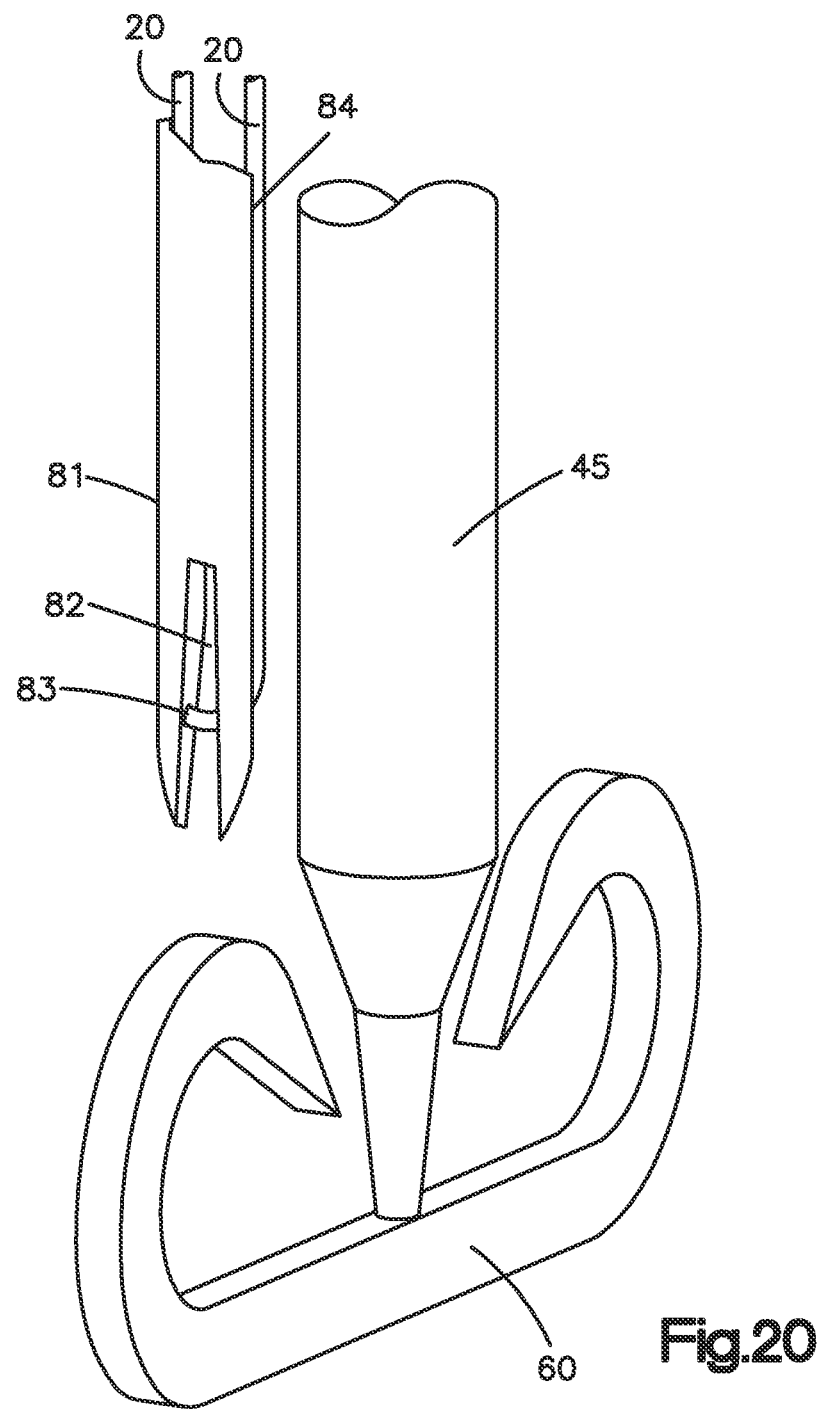

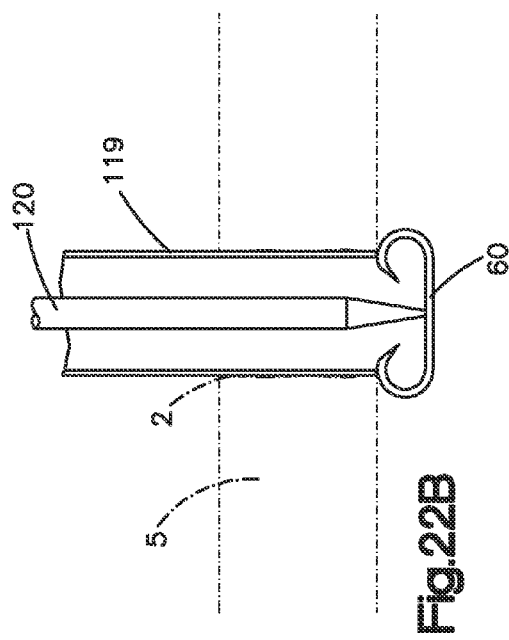
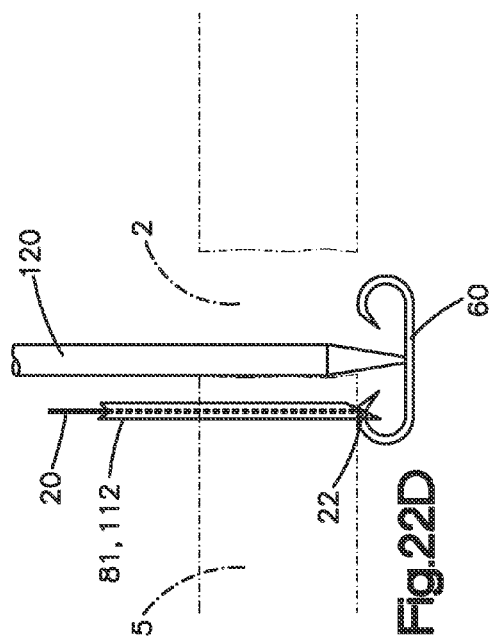
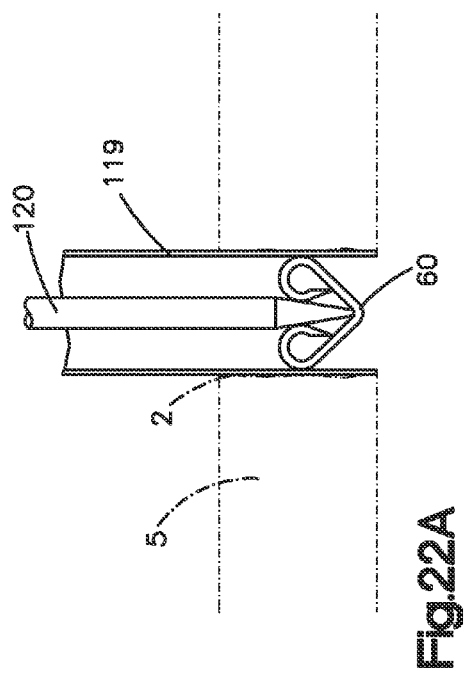
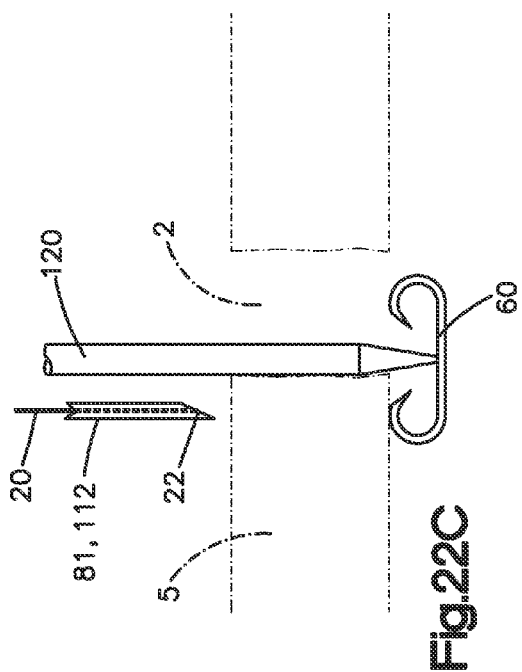

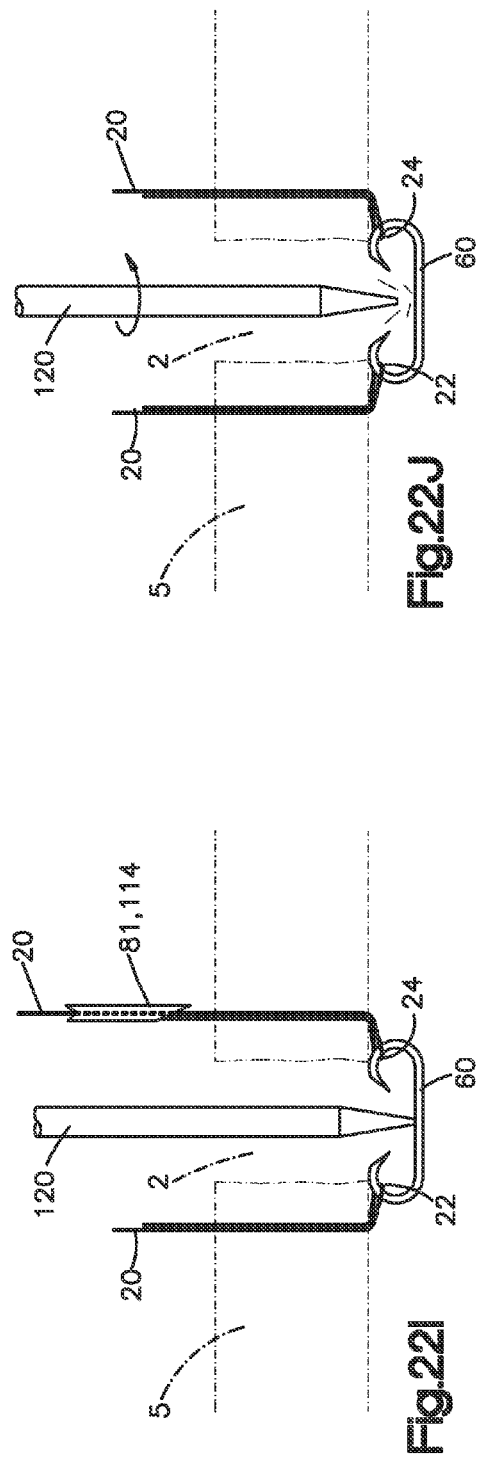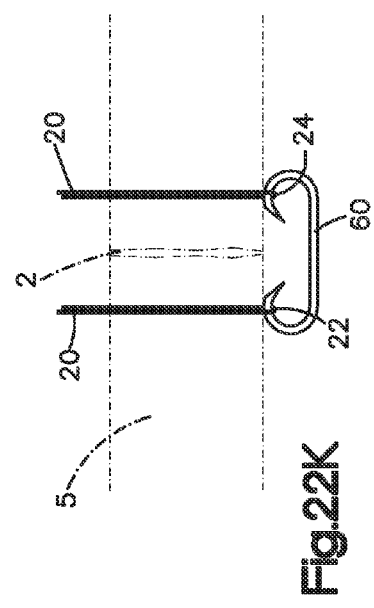

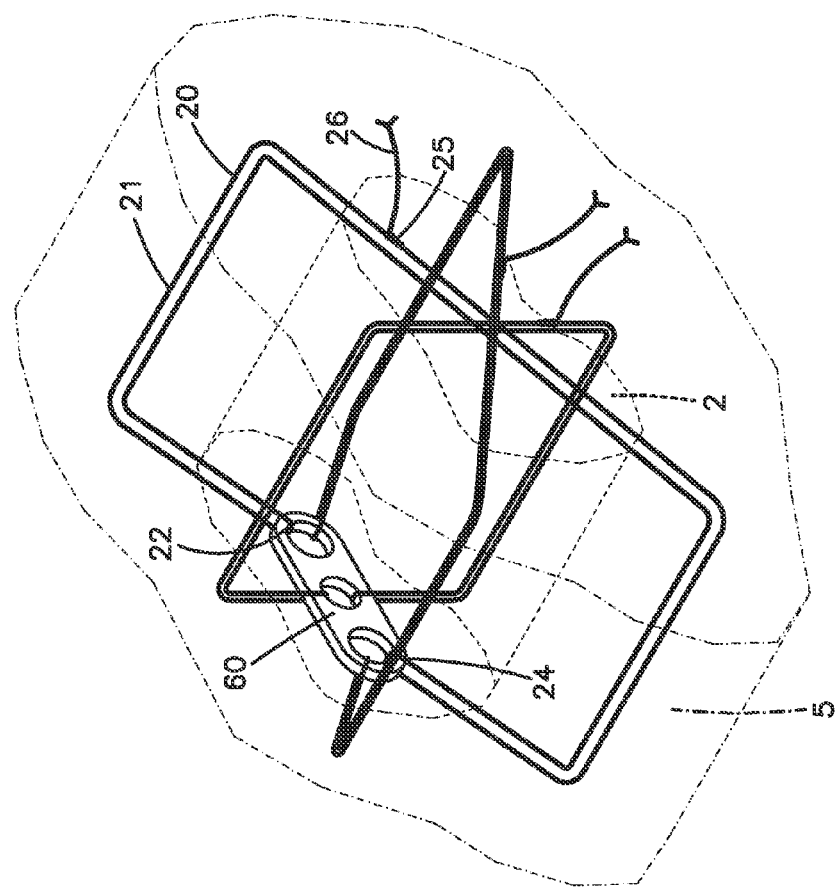
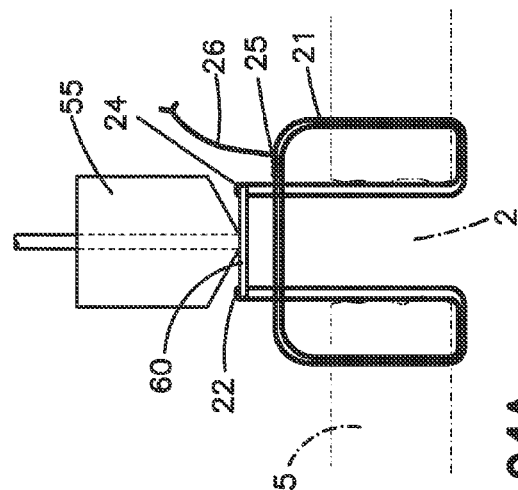
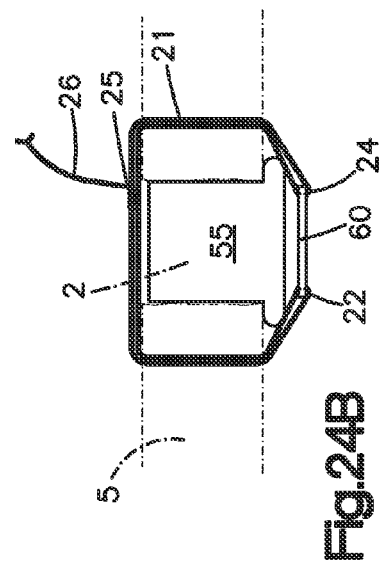

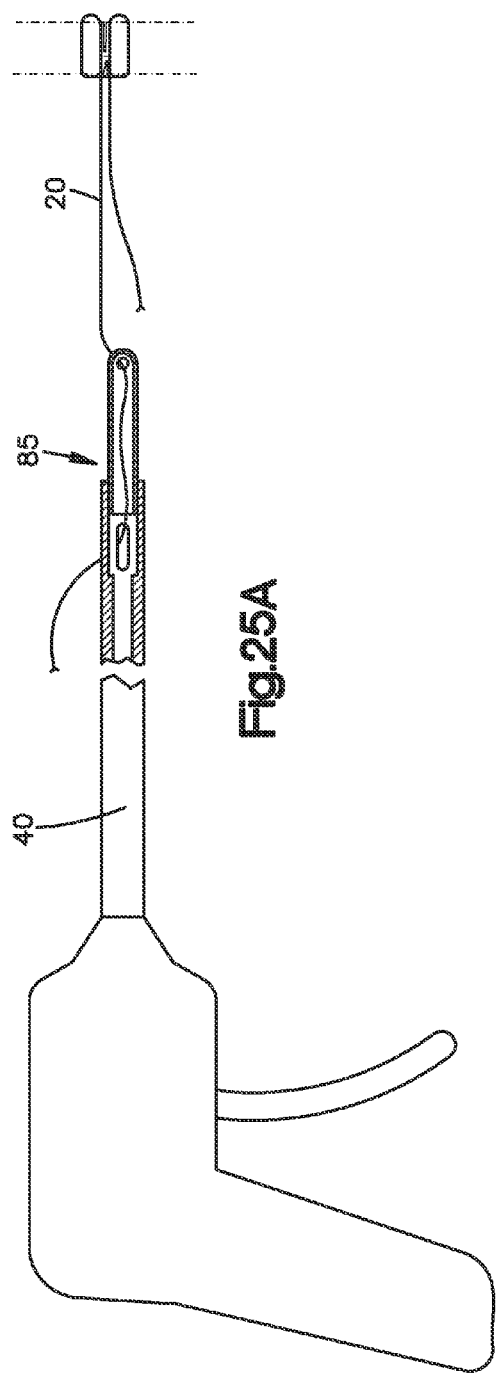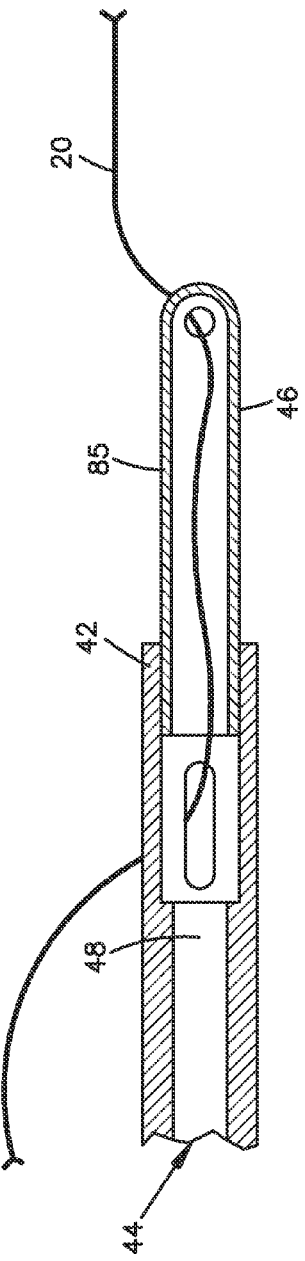

SUTURE BASED TISSUE REPAIR

CROSS-REFERENCE TO RELATED APPLICATIONS

This application is the National Stage of International Application No. PCT/US2009/046624, filed Jun. 8, 2009, which claims the benefit of U.S. Provisional Application No. 61/059,584, filed Jun. 6, 2008, the disclosures of which are incorporated herein by reference in their entireties for all purposes.

BACKGROUND OF THE INVENTION

Sciatica, or radicular leg pain, is suffered by millions of Americans. One common cause of sciatica is ruptured or herniated discs of the spine for example, in the lumbar area. That is, when the outer wall of an intervertebral disc (i.e., the annulus fibrosis) becomes weakened, it may tear allowing the soft inner part of the disc (i.e., the nucleus pulposus) to push its way out. Once the nucleus pulposus extends out past the regular margin of the annulus fibrosis, the nucleus pulposus can press against very sensitive nerve tissue in the spine resulting in radicular pain. One treatment for relieving radiculopathy is a discectomy. A discectomy is a surgical procedure performed to remove at least a part of the damaged disc to relieve the pressure on the nerve tissue and alleviate the pain. The surgery generally involves a small incision in the skin over the spine, removal of some ligament and bone material to access the disc and the removal of some of the disc material, e.g., removing herniated nucleus pulposus to achieve neural decompression. Currently, standard discectomy techniques do not repair the defect or incision in the annulus fibrosis. As a result, the remaining nucleus pulposus may extend or push its way out of the opening or damaged annulus fibrosis post-operatively. Alternatively the surgeon may elect to perform extensive debulking, in which most of the remaining nucleus material is removed in addition to the herniated portion to minimize the risk of post-operative reherniation, but this increases the risk of post-operative disc height collapse and subsequent progression to increased lower back pain.

Thus there remains a need to provide a tissue repair system and method and more specifically an annulus fibrosis repair system and method to solve the challenges present in current discectomy procedures and the post-operative complications associated therewith.

BRIEF SUMMARY OF THE INVENTION

The present invention provides an apparatus for suture-based tissue repair, including repairing a defect or opening in the annulus fibrosis of a spinal disc, that comprises a suture loop preferably pre-tied with a sliding knot, and a clasp-type component that captures the ends of the suture loop. An optional plug member that fills the opening in the annulus fibrosis may also be included. Also disclosed is a method that places the suture loop in a full-thickness stitch encircling the annulus defect, secures the ends of the suture loop to the clasp, and cinches the suture loop to approximate the annular tissue without the need to tie knots. Also disclosed is a suture passer that enables a suture strand or loop to be passed through the annulus wall, captured, and retrieved. The suture passer may optionally incorporate a clasp in such an arrangement that enables a suture loop passed through the annulus wall to be captured directly by the clasp.

In one embodiment a system for spinal disc annulus repair is provided which comprises a strand of suture and a clasp device. The suture preferably has at least one loop and at least one sliding knot, and the clasp device preferably has at least one eyelet. The eyelet may comprise a closed ring, a C-shape, a U-shape, an S-shape, an O-shape, a coil shape, or other shape having an opening to permit a suture to pass into the eyelet. The system may further comprise a suture passer and retriever instrument that may include a needle having a receptacle for receiving the suture.

In another embodiment a further system for repairing a defect in the annulus of a spinal disc is provided that may comprise a strand of suture and a clasp device having an eyelet for securing the suture. The suture may have at least one loop having two ends and a sliding knot, and the eyelet of the clasp device may be configured for securing the ends of the suture loop, wherein the suture and clasp device are configured and arranged in combination to surround the annulus defect and approximate the defect with the two ends of the loop extending in opposite directions from the clasp device. The suture and clasp device preferably are in series in forming a loop surrounding the defect of the annulus fibrosis. The system may further comprise a suture passer and retriever instrument. The suture passer may include a needle releasably attached to the suture and preferably for passing the suture through the disc annulus. The retriever instrument is preferably configured to cooperate and preferably work in association with the needle.

The suture passer and retriever instrument may further comprise a boom arm for capturing the suture. The suture passer and retriever instrument may be releasably coupleable to the clasp device. The system may further comprise a plug member for filling and sealing the annulus defect. The system may further comprise a plurality of barbs, one barb connected to each of the ends of the suture loop, and wherein the clasp device has a plurality of eyelets, each eyelet connectable to the barbs, wherein the eyelet is expandable and at least a portion of the barb is configured to pass through the eyelet. Alternatively or additionally, the suture passer and retriever instrument may comprise a wire loop for capturing the suture.

The clasp device may include a two piece clip, the first piece connectable to a first end of the suture loop, a second piece of the clip connectable to a second end of the suture loop, and the first piece coupleable to the second piece. The clasp device may have two hooks having open slots to receive the suture, the hooks being resiliently flexible to collapse to a smaller size and expand to a larger size. The suture passer and retriever instrument may further comprise two needles, each needle connectable to an end of the suture loop and being independently moveable, the clasp device releasably connectable to the suture passer and retriever instrument, the clasp device having an opening for receiving the suture.

In another embodiment, a method of repairing a defect in an annulus of a spinal disc is provided, the method comprising the steps of: (1) providing a suture having at least one loop and a sliding knot; (2) providing a clasp device for capturing the ends of the suture loop; (3) providing a passing device for attaching to the suture loops, the passing device for passing the suture through a wall of the annulus; (4) attaching a first end of the suture loop to the passing device; (5) inserting the passing device with the suture loop end through the disc annulus wall; (6) inserting the second end of the suture loop through the disc annulus wall; (7) connecting the first end and second end of the suture loop to the clasp device while the suture loop ends and clasp device are outside the spinal disc; (8) inserting the clasp device through the annulus defect so that the suture loop and clasp device form a continuous loop around the annulus defect; and (9) tightening the suture to tension the suture loop to close the defect, wherein the clasp device and suture loop are in series with each other and both the suture and clasp device approximate and draw the defect closed.

The method may further include the passing device comprising a needle and the further step of releasably attaching the needle to the suture loop. The method may further include the steps of coupling the passing device to the clasp device, and releasing the clasp device from the passing device. The method may further comprise the steps of: (1) inserting the first end of the suture loop through the annulus wall from the outside to the inside of the disc; (2) retrieving the first end of the suture loop through the defect in the annulus so that the first end of the suture loop is outside the disc space; (3) inserting the second end of the suture loop from the outside to the inside of the disc; and (4) retrieving the second end of the suture loop through the defect in the annulus so that the second end of the suture loop is outside the disc space. The method may further comprise using a multi-piece connectable clip, and connecting a first piece of the multi-piece clip to a second piece of the multi-piece clip. The method may further comprise: connecting a first end of the suture loop to the first piece of the multi-piece clip; and connecting a second end of the suture loop to the second piece of the multi-piece clip.

It should be understood, however, that the system, kit and method of use is not limited to the precise arrangements, structures, features, embodiments, aspects and instrumentalities shown, and that the arrangements, structures, and features disclosed herein can be used singularly or in combination with other arrangements, structures, features, aspects and instrumentalities.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the system, device and method of the present application, there is shown in the drawings preferred tissue repair systems, embodiments and techniques. It should be understood, however, that the application is not limited to the precise arrangements, structures, features, embodiments, aspects and instrumentalities shown, and that the arrangements, structures, features, disclosed herein can be used singularly or in combination with other arrangements, structures, features, aspects and instrumentalities. In the drawings:

FIG. 1 illustrates an embodiment of a preformed suture loop that may be used in the present invention;

FIG. 2 illustrates a perspective view of an open ring suture clasp in accordance with the present invention.

FIG. 3 illustrates a perspective view of a closed ring suture clasp in accordance with the present invention.

FIG. 4 illustrates a double eyelet suture clasp in accordance with the present invention, and an embodiment of an insertion instrument.

FIG. 5A-E illustrates a tissue repair system and method in accordance with the present invention.

FIG. 6 illustrates an alternate tissue repair system and method in accordance with the present invention.

FIG. 7 illustrates an additional method step used with the alternate tissue repair system and method shown in FIG. 6.

FIG. 8 illustrates an additional method step used with the alternate tissue repair system and method shown in FIG. 6.

FIG. 9 illustrates an additional method step used with the alternate tissue repair system and method shown in FIG. 6.

FIG. 10 illustrates an additional method step used with the alternate tissue repair system and method shown in FIG. 6.

FIG. 11 illustrates an additional method step used with the alternate tissue repair system and method shown in FIG. 6.

FIG. 14 illustrates an additional method step used with the alternate tissue repair system and method shown in FIG. 12.

FIG. 15 illustrates an additional, and preferably last, method step used with the alternate tissue repair system and method shown in FIG. 12.

FIG. 16 illustrates yet another alternate tissue repair system and method in accordance with the present invention.

FIG. 19A-F illustrates an alternative tissue repair system and method in accordance with the present invention;

FIG. 20 illustrates an alternative tissue repair system in accordance with the present invention;

FIGS. 22A-K illustrates an alternative method for tissue repair using the systems of FIGS. 20 and 21.

FIG. 23 illustrates a tissue repair system and method that includes a clasp with multiple suture loops, in accordance with the present invention.

FIG. 24A-B illustrates a tissue repair system and method that includes a plug, in accordance with the present invention.

FIG. 25A-D illustrates a tissue repair system and method that includes a knotless suture in accordance with the present invention.

DETAILED DESCRIPTION OF THE INVENTION

Figure 12:
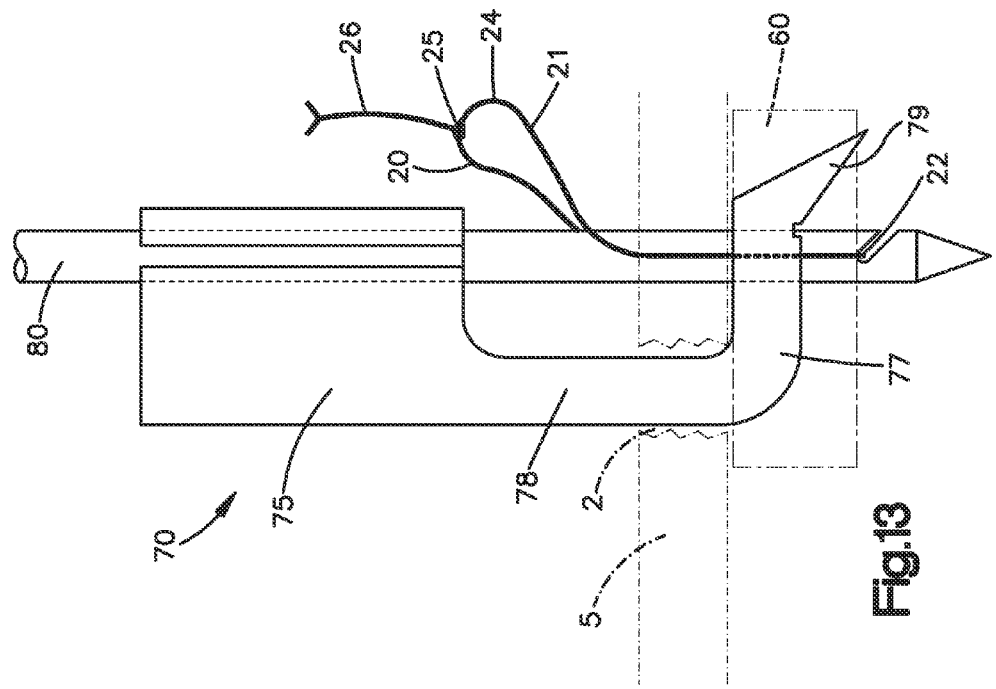
FIG. 12 illustrates another alternate tissue repair system and method in accordance with the present invention.
Figure 13:
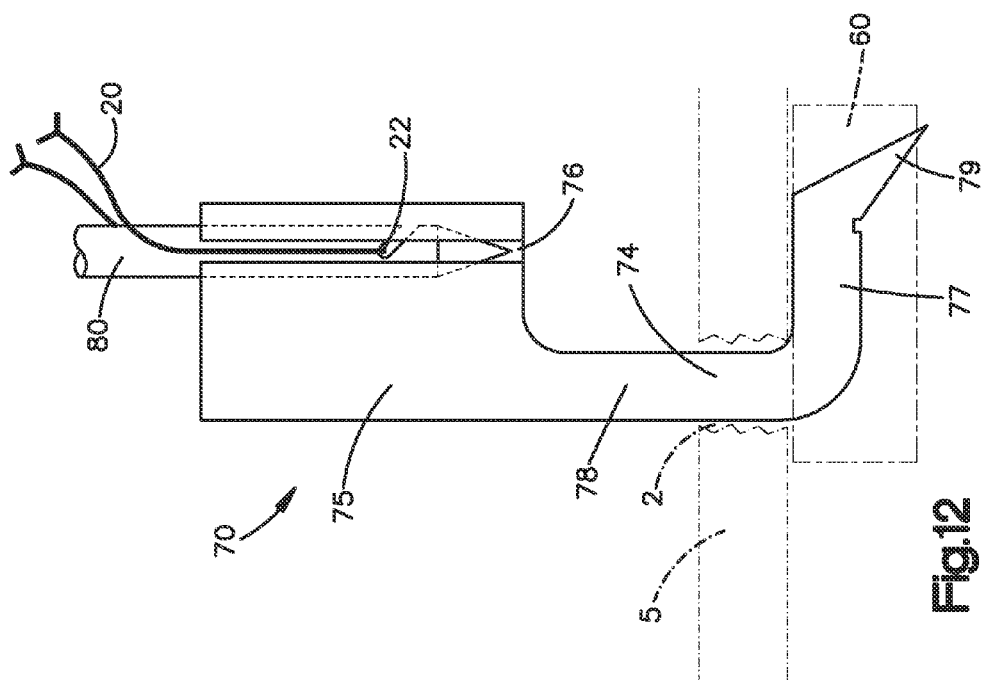
FIG. 13 illustrates an additional method step used with the alternate tissue repair system and method shown in FIG. 12.

Certain terminology is used in the following description for convenience only and is not limiting. The words "right", "left", "lower", "upper", "top", and "bottom", designate directions in the drawings to which reference is made. The words "inwardly" or "distally" and "outwardly" or "proximally" refer to directions toward and away from, respectively, the geometric center of the intervertebral space. The words, "anterior", "posterior", "superior", "inferior", "lateral" and "medial" and related words and/or phrases designate preferred positions and orientations in the human body to which reference is made and are not meant to be limiting. The terminology includes the above-listed words, derivatives thereof and words of similar import.

While the tissue repair system and method will be shown and described with reference to repairing a defect in the annulus fibrosis of a spinal disc it should be understood that the tissue repair system and method will have applicability to other bodily tissue and applications. For example, the tissue repair system and method may be used for meniscal repair, rotator cuff repair, gastroplication procedures, inguinal hernia repair, dural repair, etc. Moreover, the tissue repair system and method may be used for fixation of an implant to soft tissue, such as, for example, suture fixation of adhesion barriers, hernia meshes, rotator cuff patches, etc. In addition, while reference is often made to a defect in the annulus fibrosis of a spinal disc, or annulus defect, the tissue repair system and method is not limited in its application to annulus defects but applies to any incision, opening, wound, herniation, damage or defect in the annulus fibrosis of a spinal disc or bodily tissue. The term "annulus defect" or "tissue defect" and words of similar import should be given a broad, as opposed to a limited, interpretation to cover all such applications unless indicated otherwise.

A tissue repair system and method is provided, preferably an annulus repair system and method, that preferably includes a suture and a suture clasp. The suture 20, as shown in FIG. 1 is preferably a loop 21 of suture material pre-tied with a knot 25 which, in various embodiments can include any type of sliding knot, ratcheting knot, or locking knot now or hereafter known in the art. In a preferred embodiment, the knot is a ratcheting and/or locking knot that prevents post-operative loosening of the repair construct. The suture preferably includes a first loop end 22, a second loop end 24, and a free length of suture strand 26 adjacent to and extending from the knot 25. In this embodiment, one of the free suture strands 27 is preferably cut adjacent to the knot during manufacture. Alternatively, both free strands extending from the knot can remain, thus allowing the user to tension both strands upon final tissue approximation to promote additional locking of the knot. While the suture 20 may be supplied to the hospital, operating center or operating room with a pre-formed or pre-tied knot and loop, the suture 20 may also be configured in the operating room before or during the surgery to include a loop 21, first loop end 22, second loop end 24, knot 25 and free strand 26.

The clasp 60, in one embodiment as best shown in FIG. 2, is preferably a simple ring 61 of biocompatible material with a slot 62 configured to allow one or more loops of suture material to be secured to the clasp. In one embodiment, the clasp preferably includes a slot 62 that provides the open ring clasp in a C-shape, while in alternate embodiments, the clasp may include a carabiner-type mechanism or spring-loaded retractable sliding member 63 that enables the clasp to open and secure one or more suture loops and then close to form a closed ring configuration. The suture clasp may assume the form of the open ring suture clasp 61 as shown in FIG. 2, or may assume the form of a closed ring suture clasp 65, as best shown in FIG. 3, or may assume the form of a double eyelet suture clasp 51, as best shown in FIG. 4 and described in detail below. The suture clasp may also be U-shaped, S-shaped, C-shaped, O-shaped, coil shaped, or any other shape that has an opening to permit the loop end of a suture to pass into and be secured to the clasp.

Referring to FIG. 3, clasp 65 has a closed eyelet loop 66 and two lateral integrated cleats 67, 69. In use, the suture 20, and more specifically loop end 22, is passed through the opening 68 in the eyelet loop 66, looped over the cleat 69, and cinched tight to attach the suture loop end 22 to the clasp 65. The other suture loop end 24 is passed through the opening 68 in the eyelet loop 66, looped over the cleat 67, and cinched tight to attach suture end 24 to the clasp 65. Suture loop 24 may additionally or alternatively be passed over cleat 69 holding suture loop 22. Suture clasp 65 may be used with multiple sutures 20, or each suture strand 20 may use a single suture clasp 65.

Referring to FIG. 4, another embodiment of a suture clasp device 51 is provided. The clasp 51 features two oppositely arranged eyelets 52, 54, wherein each eyelet includes a slot 53 through which each end 22, 24 of a suture loop 21 can be routed, preferably such that the final suture loop-clasp construct is a continuous band. The slots 53 can be permanently or temporarily opened to permit the suture loop end to pass within the eyelet. Temporary opening of the slot 53 can be accomplished with a variety of mechanisms, such as a spring-loaded sliding actuate member (similar to a jewelry clamp), a spring-loaded hinged flap (similar to a carabiner), or a hingless elastic eyelet that allows the slot 53 to open under load and close thereafter. These same mechanisms can be utilized in clasps 61 or 65. In use the suture loop end 22 may be inserted through slot 53 in eyelet 52 while the suture loop end 24 may be inserted through slot 53 in eyelet 54 to attach the two ends of the suture loop to the clasp 51. Suture clasp 51 may be used with multiple sutures 20, or each suture strand 20 may use a single suture clasp 51.

A system and method for repair of a disc annulus using a suture 20 and clasp 60 is illustrated in FIGS. 5A-E. Clasp 60 may be any one of clasps 51, 61 and 65 shown and described in FIGS. 2, 3 and 4, or alternative clasps may also be used. In use, a suture, such as, for example, the suture 20 illustrated in FIG. 1, is preferably provided that is pre-tied to include a ratcheting, locking, or other sliding knot 25 such that the suture includes a first loop end 22, a second loop end 24, and a free length of suture strand 26 adjacent the knot 25. As shown in FIG. 5A the first loop end 22 of the suture is passed through the annulus wall 5 into the interior 3 of the disc 1 on a first side of an annulus defect 2 while the other end 24 of the suture, including the suture knot 25 and the free strand 26 of suture, remain external 6 to the annulus wall 5. The first loop end 22 of the suture 20 is then retrieved through the annulus defect 2 and held exterior 6 to the annulus wall as shown in FIG. 5B.

The second loop end 24 of the suture 20 as shown in FIG. 5C is then passed through the annulus wall 5 into the interior 3 of the disc 1 on a second side of the annulus defect 2 while the first loop end 22 of the suture, the suture knot 25, and the free strand 26 of suture 20 remain external 6 to the annulus 5. As shown in FIG. 5D, the second loop end 24 of the suture is then retrieved through the annulus defect 2 and held exterior 6 to the annulus 5 and adjacent the first loop end 22. The clasp 60 is then used to join the first and second loop ends 22, 24. The free strand 26 of suture is then pulled, whereby the clasp 60 and the two loop ends 22 are drawn into the interior 3 of the disc and the annulus defect or opening 2 is approximated and closed as shown in FIG. 5E. Alternatively, the clasp 60 may be advanced into the interior of the disc first, then the free strand 26 of suture 20 is pulled to approximate the annulus defect. The free strand 26 of suture may then be trimmed. The suture can be passed through the body tissue with a needle or other known suture insertion device, or the devices described herein. In the method of FIGS. 5A-E, the suture loop is passed from the outside or exterior of the disc annulus to the interior of the disc space and thereafter retrieved through the defect so that the suture can be connected to the clasp while both the clasp and suture are exterior to the disc space, and preferably exterior to the patient.

Referring to FIG. 4, an inserter 50 is provided that enables a surgeon to advance the clasp 51 manually through an annulus defect. The inserter 50 is connected to the clasp, for example, via a threaded interface. The inserter optionally may be cannulated to accept the suture strand(s) and allow cinching of the construct for tissue approximation. In the technique used with inserter 50, the ends 22, 24 of the suture loop 21 are passed through the thickness of the annulus wall 5 from outside to inside and the loops 22, 24 are retrieved through the opening 2 in the annulus as described in the method of FIG. 5. With the loop ends 22, 24 exterior to the disc space, the loop ends are hooked to the clasp 51 by inserting the loop ends 22, 24 through the slots 53 in the eyelets 52, 54. The free end 26 of the suture strand is passed up the cannulated shaft of the inserter 50. The clasp inserter 50 with connected suture loops ends 22, 24 is advanced through the defect 2 in the annulus wall 5 and the free end 26 of the suture is pulled to cinch up the loop 21 and draw the ends of the opening in the annulus together. The inserter 50 is detached from the clasp (e.g., unthreaded) and the free strand 26 of the suture 20 is cut as desired. Alternatively, the free strand 26 and knot 25 may be positioned external to the disc as shown in FIGS. 11, 15, 18, and 17. The inserter 50 can be optionally used in conjunction with the methods shown in FIGS. 5-11, or other methods described herein.

In the tissue repair system and method of FIGS. 5A-E, the clasp is in series with the suture loops and forms a continuous strand of suture. Without the clasp in FIGS. 5A-E the suture would not approximate and close the tissue defect. The system and technique of FIGS. 5A-E have particular application to a surgical site deep within the body. The suture is reapproximated to the clasp and the clasp and suture in combination cinches and reapproximates the defect (i.e. draws the tissue defect closed). One advantage of the tissue repair system and method is the use of pre-tied sutures which form a loop as shown in FIG. 1. Pre-tied sutures facilitate the speed and increases the reliability of the wound closure since a surgeon will not need to form knots with suture strand in a surgical environment and deep within a patient. In a surgical environment where (1) the surgeon is working with surgical gloves, (2) the wound is deep within a patient, (3) the openings to the surgical site are minimized to facilitate speedy recovery and (4) the surgical site has blood and other bodily tissue and fluids making visibility and manual dexterity difficult, tying and manipulating suture strands can be difficult, and the use of pre-tied sutures may be advantageous.

A tissue repair system and method is provided in FIGS. 6-11 that may have particular application to repairing a spinal disc annulus, or other body tissue, and that preferably includes a suture 20, a suture passer/retriever instrument 70, and a suture clasp 60. The suture may be as illustrated in FIG. 1, and the clasp 60 may be any one of clasps 51, 61 and 65 shown in FIGS. 2-4, or other clasps that connect the ends of the suture loop. The suture passer/retriever instrument 70 may be configured to allow a suture loop 21 to pass through an annulus wall 5 on either side of a defect 2 from the external side 6 of the annulus wall to the interior side 3 of the annulus wall 5. The suture passer/retriever instrument 70 may also be configured to retrieve the passed suture loop end 22 from within the interior of the disc to enable a surgeon to secure the suture loop 21 to a clasp 60 located external to the disc space 3. In alternate embodiments discussed in more detail below, the clasp can be loaded into or onto the suture passer/retriever instrument such that the suture loop 21 can be passed through the annulus wall to the interior of the disc space and captured directly by the clasp while within the interior of the disc space.

The suture passer/retriever instrument 70 includes a frame or housing 75 which further includes a proximal portion 72 (not shown), a distal portion 74 and a longitudinal axis 71 extending therebetween. The proximal portion of the suture passer/retriever instrument 70 includes a cannulated portion 76 configured to house and direct the movement of a needle 80. The needle 80 has an open slot (see FIG. 20) through which is passed a strand of the suture 20. The distal portion 74 of the suture passer/retriever instrument 70 is configured for placement through the disc annulus defect and into the interior 3 of the disc space. The distal portion 74 may be characterized by a thin portion 78 that is sized and configured for introduction through an annulus defect and a laterally extending boom arm 77. The boom arm 77 may also include a distally extending obliquely oriented tip 79, as is best shown in FIG. 6, that is sized and configured to retrieve the suture once inside the disc space. The boom arm 77 may include a latch or hook that would catch and retain the suture loop as the needle is withdrawn from the disc annulus. The suture passer/retriever instrument 70 is unidirectional in that the suture only passes in one direction through the disc annulus.

In use, and with reference to FIGS. 6-11, the first end 22 of the suture loop 21 is preferably secured to the needle 80 seated within the frame 75 of the suture passer/retriever device 70 and the distal end 74 of the suture passer/retriever device 70 is inserted into the interior 3 of the disc space through a defect 2 within the wall 5 of the annulus, as best shown in FIG. 6. The needle 80 carrying the first end 22 of the suture loop 21 then moves through the annulus wall 5 on one side of the defect while the second end 24 of the suture loop 21, knot 25, and free strand 26 of the suture are retained outside of the disc space, as best shown in FIG. 7. The needle 80 is then retracted back into the housing 75 of the suture passer/retriever device 70 while, the first end 22 of the suture loop 21 is captured by the boom arm 77. The suture passer/retriever device 70 (with the suture loop 21 captured by the boom arm) then is withdrawn from the disc space 3 through the annular defect 2, as best shown in FIG. 8. The first end 22 of the suture loop 21 is then removed from the suture passer/retriever instrument 70 and is held outside of the disc space.

The second end 24 of the suture loop 21 is secured to the needle 80 and the distal end 74 of the suture passer/retriever device 70 is reinserted into the interior 3 of the disc space through the annulus defect. The suture passer/retriever instrument 70 is manipulated so that the boom arm 77 is located beneath the other side of the annulus defect where the user desires to pass the suture. The needle 80 carrying the second end 24 of the suture loop 21 then translates distally and is guided through the annulus wall 5 on the other side of the annulus defect 2 while the first end of the suture loop 22, knot 25, and free strand 76 of suture are retained outside of the disc space, as best shown in FIG. 9. As best shown in FIG. 10, the needle 80 is withdrawn proximally back towards the housing 75 of the suture passer/retriever device 70 and, the second end 24 of the suture loop is captured by the boom arm 77. The suture passer/retriever device 70 with the captured suture loop end 24 then is withdrawn from the disc space through the annulus opening. A suture clasp 60, such as either of the suture clasps 51, 61, 65 shown and described in reference to FIGS. 2-4, or other clasp type is used to join the first and second ends 22, 24 of the suture loop 21. The free strand 26 of the suture is then pulled, which can in one example be facilitated by using a knot pusher known in the art for use with sliding suture knots, whereby the suture clasp 60 and the two loop ends 22, 24 are drawn into the interior 3 of the disc 1 and the annulus defect 2 is approximated, as is best shown in FIG. 11.

Alternatively, the clasp 60 and loop ends 22, 24 may be advanced into the interior 3 of the disc first, and then the free strand 26 of suture is pulled to approximate the annulus defect. The free strand 26 of suture is then trimmed, while the knot 25 is exterior to the annulus. Alternatively, or additionally, the knot may be fully recessed by advancing it into the annulus, for example, down one of the needle tracts during cinching.

In the system and method of FIGS. 6-11, the suture loop is passed from the outside of the disc annulus into the interior of the disc space and thereafter retrieved through the disc annulus defect so that the suture can be connected to the clasp while both the clasp and ends of the suture loop are exterior to the disc space, and preferably exterior to the patient so that the suture can be easily handled and connected to the clasp. In the tissue repair system and method of FIGS. 6-11, the clasp is in series with the suture loop and forms a continuous strand of suture. The suture loop is connected to the clasp, and the suture in combination with the clasp cinches and reapproximates the tissue defect. Without the clasp in the method of FIGS. 6-11, the suture would not reapproximate the tissue defect.

Referring to FIGS. 12-15, a tissue repair system and method is provided that preferably includes a suture loop 21 with pre-tied knot 25 as described previously, a suture passer/retriever instrument 70, and suture clasp 60 preloaded onto the suture passer/retriever instrument, thereby saving procedural effort and time. The clasp 60 may be threaded onto, snap fit, or connected to the boom arm 77 by other methods. Preferably the clasp 60 is configured similar to the open ring clasp 61 in FIG. 2. The method of operation of FIGS. 12-15 is similar to that described above in connection with FIGS. 6-11. During the step shown in FIG. 13, however, as the needle translates and is guided downwardly through the annulus wall on one side of the annulus defect, the first end 22 of the suture loop is hooked through the preloaded open ring suture clasp 61 secured to or within the boom arm 77. Similarly, and with reference to FIG. 14, as the needle translates and is guided downwardly through the annulus wall on the opposite side of the annulus defect, the second end 24 of the suture loop is hooked through the preloaded open ring suture clasp 61 secured to or within the boom arm 77. During the last step, and with reference to FIG. 15, the preloaded open ring suture clasp 60 is manually or automatically ejected from the suture passer/retriever instrument 70, the distal end 74 of the suture passer/retriever instrument 70 is removed from within the disc, the free strand of suture 26 is pulled, the sutures are cinched and drawn tight to close the annulus defect, and the free strand 26 of suture is trimmed. In the embodiment and method described in FIGS. 12-15 the clasp and instrument 70 remain within the annulus until both ends of the suture loop are connected to the clasp and then the instrument 70 is removed from the disc. The clasp in the embodiment and method of FIGS. 12-15 preferably remains inside the disc. A rod (not shown) may be operated by the user to push or eject the clasp from the instrument 70.

In the embodiment of FIGS. 12-15 the slots in the open ring clasp may be open when the clasp is attached to the suture passer/retriever instrument 70, and the suture passer/retriever instrument 70 may open the slots as the clasp 60 is attached to the instrument 70. Similarly the slots may close as the clasp is ejected from the suture/passer retriever instrument 70. That is, the clasp 60 may be configured so that the slots are biased or automatically closed unless held open and the suture passer/retriever instrument 70 may have a mechanism that opens and holds open the slots as the clasp is loaded onto the instrument 70. When the clasp is released from the instrument 70 the slots will automatically close.

While the suture passer/retriever instrument 70 shown and described in FIGS. 6-11, and 12-15 has been configured to have the needle associated with retaining and moving the suture from the exterior to the interior of the disc other configurations are contemplated. For example, the suture may be retained on the boom arm 77 of the suture passer/retriever instrument and the needle may pass from the exterior to the interior of the disc and as the needle is being withdrawn from the disc it will capture the suture loop and pull it back out through the annulus wall. The same method may apply to the other end of the suture loop and with both suture loop ends outside of the disc a clasp may thereafter be connected to the suture loop ends and the suture cinched and tightened to close the annulus opening in combination with the clasp.

Referring to FIGS. 16 and 17, an annulus repair system and method is provided that includes a suture loop 21 with knot 25, a suture clasp 60 similar or identical to the suture clasp 51 shown and discussed in reference to FIG. 4, and a pair of barbs 90. The suture clasp 60, suture 20, and suture barbs 90 are best shown in FIG. 17. The suture clasp 60 is preloaded onto the suture passer/retriever instrument 70, and the method is similar to that described above in reference to FIGS. 12-15.

The suture barbs 90 preferably have a stem 96 with an eyelet 97 for capturing one end of the suture loop. The barb 90 also preferably has a tip, preferably pointed for piercing and passing through the disc annulus. One of the suture barbs 92 may be connected to the first end 22 of the suture loop 21 and the second suture barb 94 may be connected to the second end 24 of the suture loop 21. The suture and barbs may be supplied preassembled and connected together and in a kit, or the suture connections with the barbs may occur before or during the procedure. With preassembled barbs where the suture loop is connected to the barb the surgeon does not have to tie knots to close the disc annulus opening potentially resulting in a faster procedure and a more reliable closure of the annulus opening. The barb may be mounted to a suture passer instrument 70 similar to the embodiments of FIG. 5-11 or 6-12 but adapted to utilize barbs 90 instead of a needle in use.

Figure 17A:
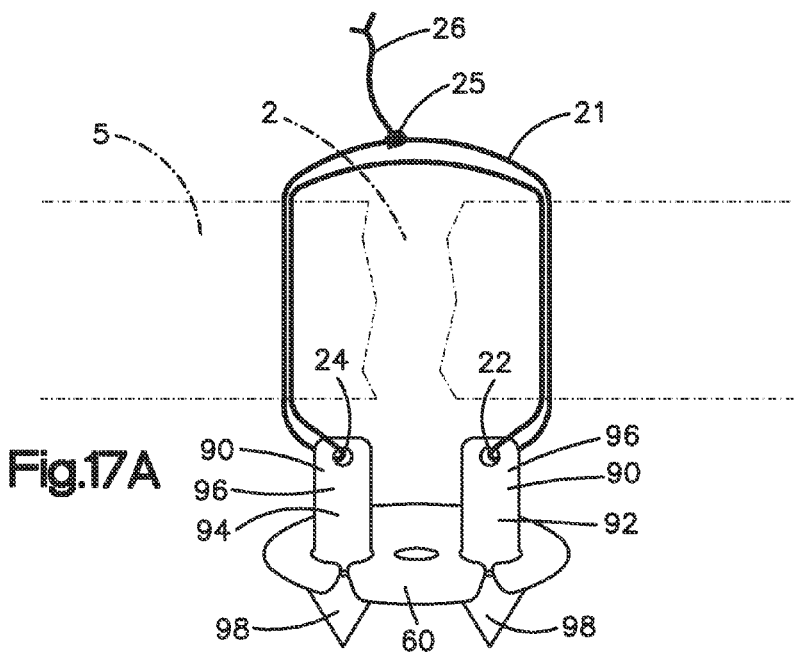
FIG. 17A-B illustrates a tissue repair system and method that includes a pair of barbs, in accordance with the present invention.
Figure 17B:
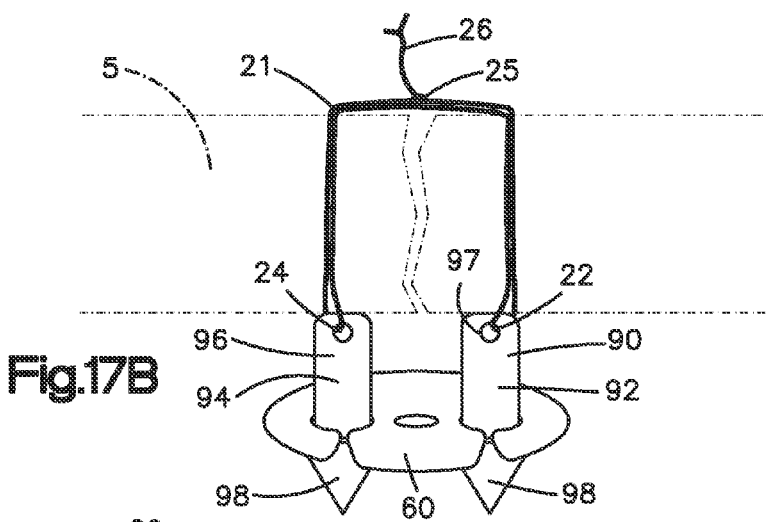

The barb 90 is moved through the disc annulus and the tip 98 of the barb 90 moves through eyelet 54 until the stem 96 of the barb is located within the eyelet. More specifically, the proximal end of the tip 98 is larger than the eyelets 52, 54 so that as tip 98 moves through the eyelet 52, 54 the eyelet as a result of slots 53 expands to a larger size to enable the tip 98 to pass through eyelet 52, 54 whereupon the stem 96 is received in the eyelet 52, 54 and the eyelet returns to its original unflexed state. The barb 90 is thereby captured by the clasp 60. The second barb 90 is inserted through the annulus of the disc at a second location and the tip 94 is passed through the eyelet 54 until the stem 96 is located within the eyelet 54. The clasp 60 is thereafter ejected from the suture passer/retriever instrument as shown in FIG. 17A. The suture loop is then tightened by pulling free strand 26 which cinches the sutures, proximating and closing the annulus defect as shown in FIG. 17B.

Depending upon the design of the barbs 90 it may or may not be desirable for the stems 96 of the barbs 90 to extend up and into the wall of the annulus. If it is undesirable for the stems of the barbs to be located within the punctures formed by the barbs upon proximating and closing the opening in the annulus, which may be desirable and necessary to achieve proper reapproximation of the defect, then care should be taken, for example, by insuring that the distance between the punctures in the annulus when the defect in the annulus is closed is greater than the distance of the eyelets in the clasp.

Figure 18:
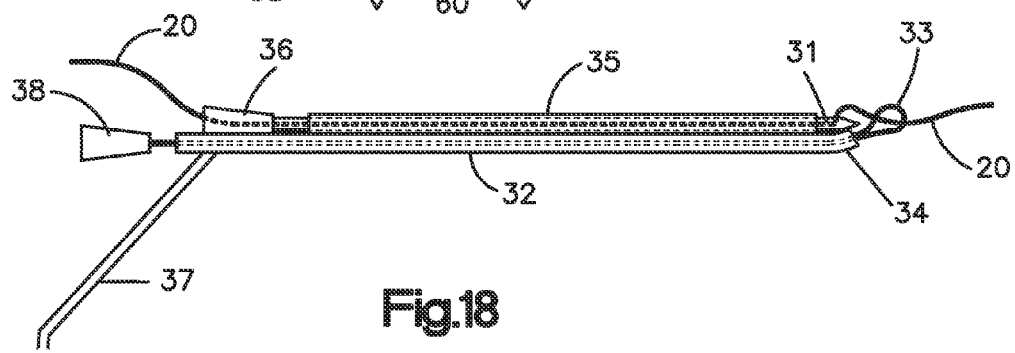
FIG. 18 illustrates an alternate embodiment of a suture passing instrument in accordance with the present invention.

Referring to FIG. 18, an alternate embodiment of a suture passing instrument is provided. The suture passer 30 of FIG. 21 includes an axially translatable suture passing needle 31 moveable within a needle housing 35 by a needle knob 36. The needle housing 35 is attached to a guide body 32. The guide body 32 has a handle 37 and also includes a lumen 34 that houses a deployable wire loop 33 configured to snare and retrieve a suture 20 passed through the annulus. The guide body 32 and lumen 34 may be angled at its distal end, preferably towards the projected path of the needle. The suture passer has a knob 38 for controlling movement of the wire loop 33 which is deployed from the distal end of the guide body 32 in such a way that it encircles or is moveable to encircle the projected path of the needle 31 and/or the passed suture to allow the passed suture to be retrieved using a "blind" technique that does not require direct visualization.

The needle 31 can be loaded with the suture loop 21. The distal end of the suture passer 30 including the angled lumen of the guide body and the wire loop 33 are inserted through the opening 2 in the annulus to be repaired and the wire loop 33 is manipulated so that it encircles the projected path of needle 31. The needle 31 is advanced through the annulus wall and through the wire loop and the wire loop is used to catch the suture 20. The needle 31 is retracted while the wire loop 33 holds the suture 20. The suture passer 30 is then removed from the annulus with the wire loop holding and retrieving the suture from inside the disc so that the suture passes out of the annulus opening. The same technique is employed with the suture passer 30 in other location(s) surrounding the annulus opening and the suture is retrieved from the interior of the disc space through the opening. The suture ends are then connected to a clasp 60, which can be any one of the clasps 51, 61, 65 shown in FIGS. 2-4, or any other clasp, and the method of cinching the sutures and closing the opening of the annulus as described and shown in FIGS. 5D-E, 11 and 15 can be employed. The guide body 32 may alternatively accommodate multiple needles or needle housings arranged about its outer diameter and corresponding deployable wire loops or a single rotationally-indexing wire loop. In one embodiment, the needle may be straight and the lumen may be angled, the lumen projecting towards the opening of the axially deployed wire loop. In another embodiment, the suture passing needle 31 may be curved at its distal end with the wire loop 33 deploying axially.

FIGS. 19A-F illustrates another embodiment of a tissue repair system and method. The tissue repair system of FIGS. 19A-F includes a suture 20, and a two-piece connector clip 35. The two piece connector clip 35 includes a first clip part 36, having a projecting portion 37, and a second clip part 38 having a receiving portion 39. The first clip part 36 attaches to the second clip part 38. The clip parts 36, 38 may be connected in many ways now known or hereafter developed including threaded connections, snap connections, interlocking flanges and shoulders, etc. Each clip part 36, 38 may further include a channel, hole or eyelet so that the suture can be attached to the clips parts 36, 38.

Figure 19A:
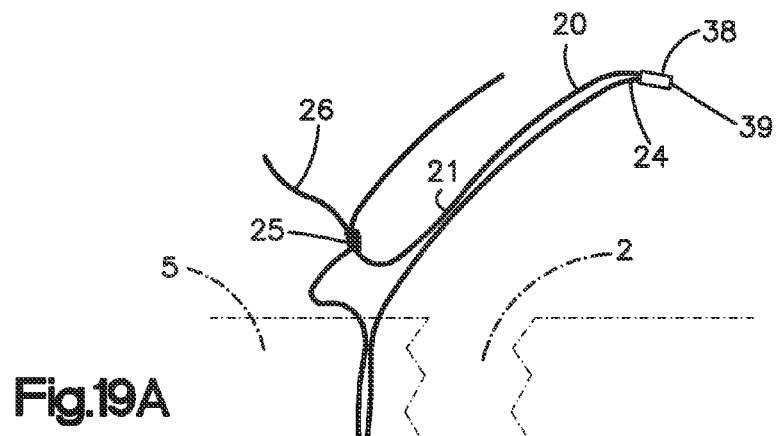
Figure 19B:
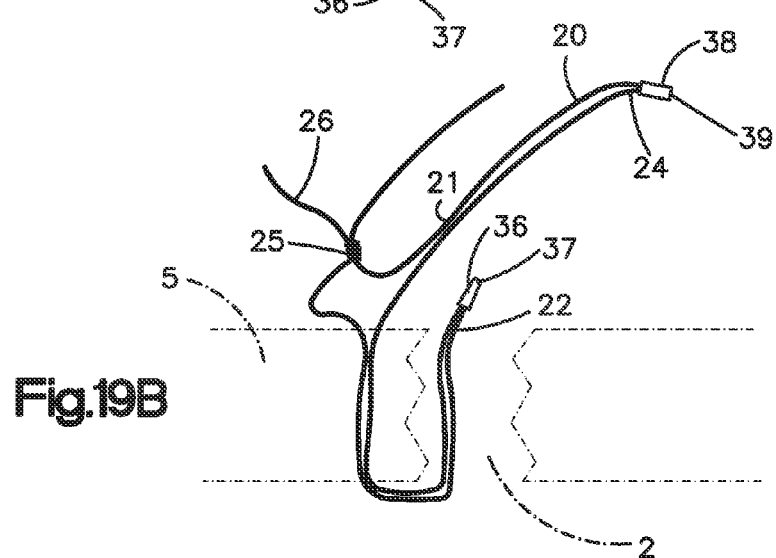
Figure 19C:
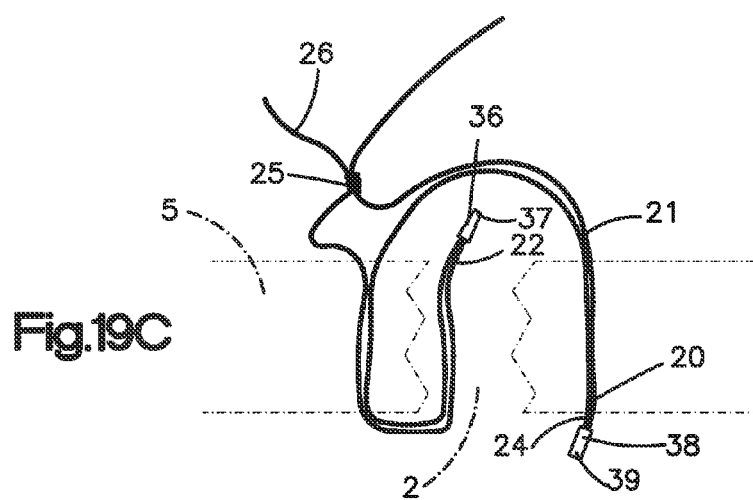

The suture 20 and two piece connector clip parts 36, 38 may be provided preassembled for the surgery where a first loop end 22 is associated with and preferably connected to the first clip part 36, and the second loop end 24 is associated with and preferably connected to the second clip part 38 forming a suture loop 21 with a pre-tied knot 25 and free length of suture strand 26. A needle (not shown) is inserted through the annulus wall 5 and the first part 36 of the clip connector 35 is passed through the annulus into the interior of the disc as shown in FIG. 19A. The suture 20 is free to slide through the hole in the first clip part 36. The first clip part 36 is retrieved through the defect in the annulus wall so that it is outside or exterior to the disc space as shown in FIG. 19B. Next the needle is inserted through the other side of the defect in the annulus and the second clip part 38 is passed through the annulus 5 as shown in FIG. 19C so that it is located in the interior of the disc. The second clip part 38 is then retrieved through the defect in the annulus so that it is outside or exterior to the disc space as shown in FIG. 19D. The two clip parts 36, 38 are clipped together preferably while located exterior to the disc space as shown in FIG. 19E, and preferably exterior of the patient, and the suture knot 25 is pulled tight so the clip 35 is drawn into the disc space as shown in FIG. 19F, and the two sides of the annulus defect are drawn tightly together. Several suture and clip assemblies 35 may be used together to repair the tear, defect, incision, or opening in the annulus of the spinal disc.

In the system and method of FIGS. 19A-E the suture loop is passed from the outside of the disc annulus into the interior of the disc space and thereafter retrieved through the disc annulus so that the clips can be connected while both the clips and ends of the suture loop are exterior to the disc space, and preferably exterior to the patient so that the suture can be easily handled and the clips connected together. In the tissue repair system and method of FIGS. 19A-F, the clips are in series with the suture loop and forms a continuous construct. The suture is connected to the clips, and the suture in combination with the clips cinches and reapproximates the tissue defect. Without the clips in the method of FIGS. 6-11, the suture would not approximate and draw the tissue defect closed.

Figure 21:
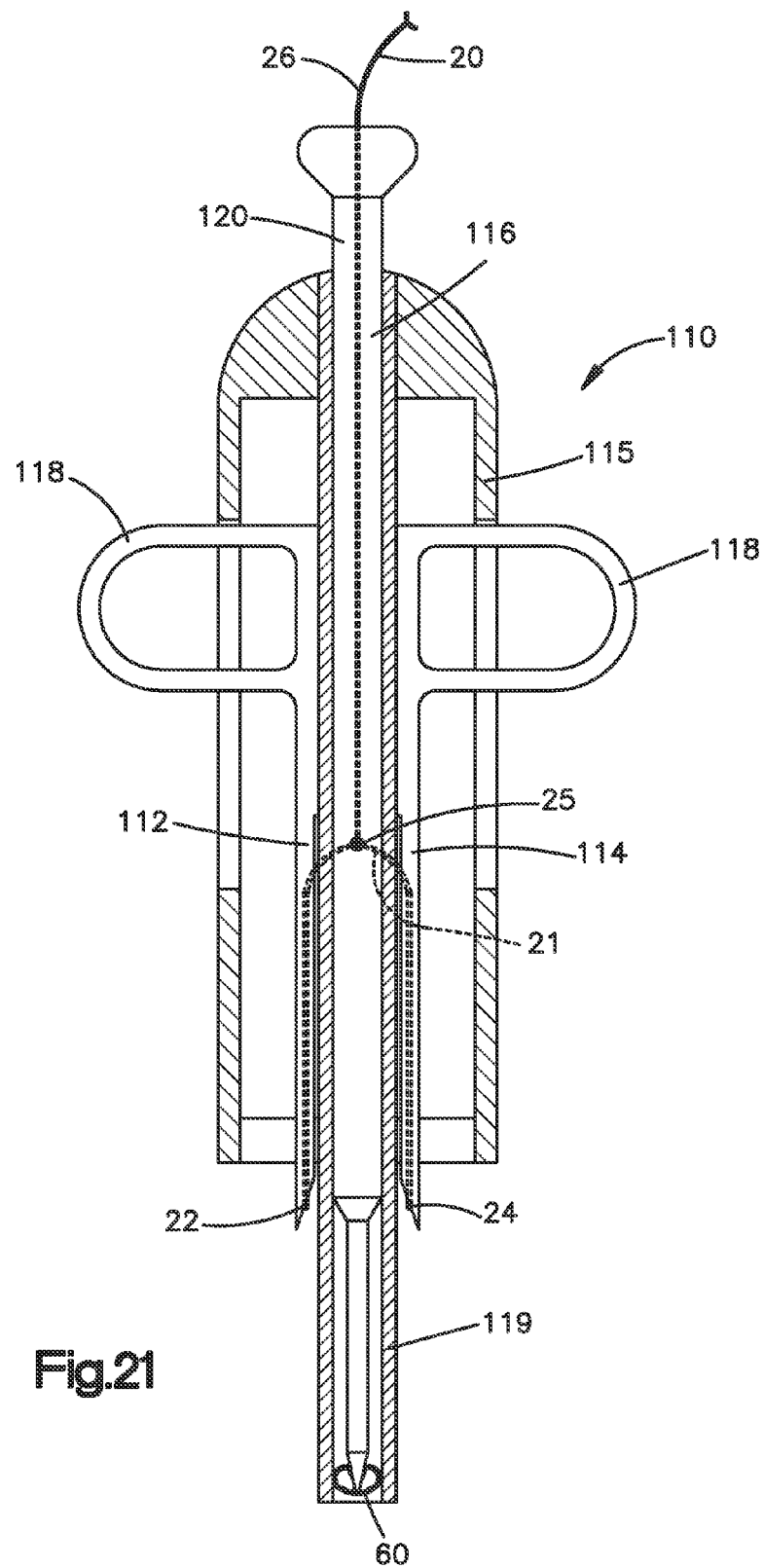
FIG. 21 illustrates an alternative tissue repair system in accordance with the present invention.

A further embodiment of a suture based tissue repair system and method is shown in FIGS. 20-22. The suture based tissue repair system of FIG. 20 includes a needle 81 configured and adapted to hold and connect to a suture 20, a clasp 60 and a clasp inserter 45. The needle 81 may be independent of the clasp 20 and clasp inserter 45 or may be part of an integrated design as illustrated and described with reference to FIG. 21. The needle has an opening or notch 82 in its distal end and a channel 83 for guiding and maintaining the suture across the needle opening. A further channel 84 may be provided to retain the suture along the length of the needle. The guide channel 83, opening 82 and clasp 60 are configured so that the suture 20 can be inserted through the slot in the clasp 60 and looped over the open end of the clasp 60.

FIG. 21 illustrates an alternative suture assembly and clasp instrument 110. The suture inserter and clasp assembly instrument 110 has a first needle 112 and a second needle 114 located within and slidable relative to housing 115. Housing 115 is cannulated and has an inserter 120 located within cannulated bore 116. The inserter 120 is moveable relative to the housing 115 and preferably slidable within bore 116 in housing 115. A clasp 60, similar to clasp 60 in FIG. 20, is connected to the distal end of the inserter 120. First needle 112 and second needle 114 each may be structured and configured similar to needle 81 in FIG. 20. A suture 20 is threaded across an opening in the first and second needles 112, 114 similar to FIG. 20. The first and second needles 112, 114 each have a handle 118 that extends through a slot located in housing 115 and are each independently operable by a user to move each respective needle relative to the housing so the distal end of the needle extends from the housing. A first loop end 22 of the suture 20 extends around the first needle 112 and a second loop end 24 of the suture 20 extends around the second needle 114. The suture knot 25 preferably is located within the housing and the free strand 26 of the suture extends out the bore 116 of the housing 115.

Figure 22E:
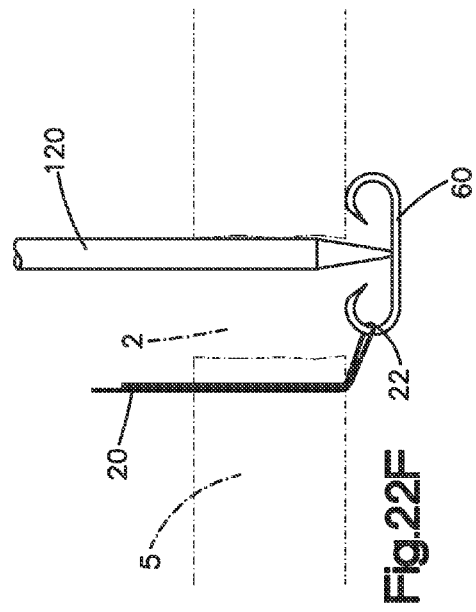
Figure 22F:
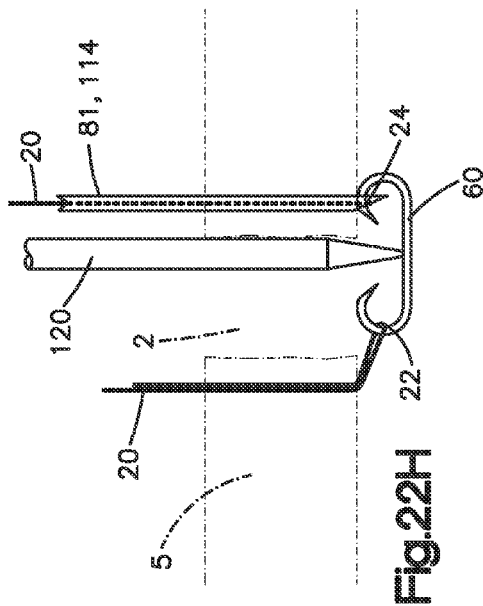
Figure 22G:
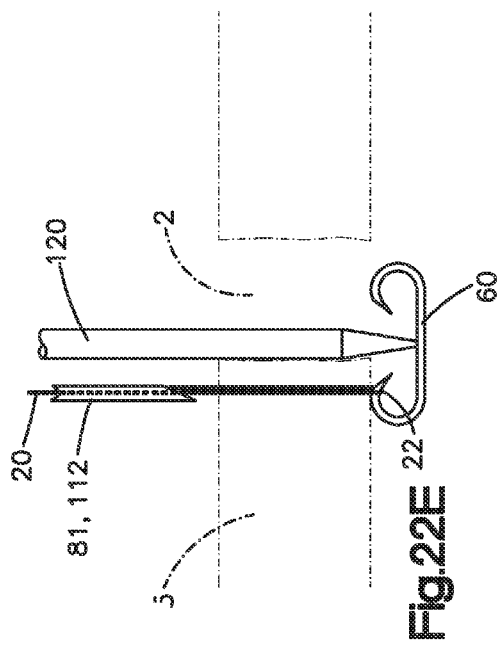
Figure 22H:
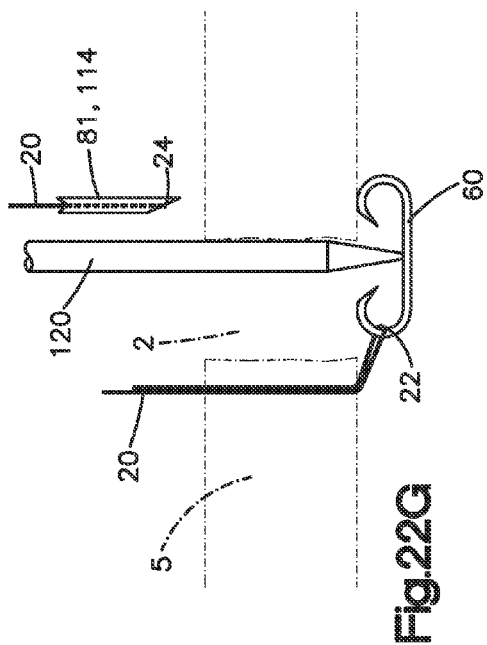

The use of the needle 81 and the clasp inserter 45 of FIG. 20, and the use of the suture inserter and clasp assembly instrument 110 of FIG. 21, is shown in FIGS. 22A-K. The inserter 45, 110 and clasp 60 is inserted through the defect in the annulus of a spinal disc. If the assembly 110 of FIG. 21 is used, the tip of the cannula 119, which houses the inserter 120 and clasp 60 assembly, is inserted through the annulus defect as shown in FIG. 22A and the inserter 120 is then moved in housing 115 so the clasp 60 extends outside the cannula 119 and into the interior of the disc space as shown in FIG. 22B. The clasp 60 preferably expands to a larger or different size as it exits the cannula 119 as shown in FIG. 22B. The inserter/clasp assembly may be moved toward the first side of the annulus as shown in FIG. 22C and the needle 81, or first needle 112 may be inserted through the annulus. Next the suture end 22 is looped over the clasp as shown in FIG. 22D and the needle 81, 112 is withdrawn from the annulus with the first loop end 22 of the suture wrapped around the clasp 60 as shown in FIG. 22E. The inserter/clasp assembly instrument 110 is moved to the other side of the annulus defect, shown in FIG. 22F, and the needle 81, second needle 114 is inserted through the second side of the annulus, shown in FIG. 22G, and the needle is moved over the clasp 60 so that the suture is hooked onto and held by the clasp as shown in FIG. 22H. The needle 81, second needle 114 is withdrawn from the annulus with the suture held by the clasp 60 as shown in FIG. 22I. The inserter 45, 120 is then disconnected from the clasp 60, shown in FIG. 22J, and the inserter is withdrawn from the annulus defect. The suture 20 is then drawn tight so that the opening in the annulus is closed and drawn tightly together and the free end of the suture is cut as desired.

The systems and methods described above can be further adapted for use with more than one suture loop, as shown in FIG. 23. In this embodiment, the ends of each suture loop could be secured by the same clasp, or optionally a separate clasp could be used for each suture loop. The suture loops could be passed through the annulus and around the annular defect in configurations known in the prior art or hereafter discovered. Examples of these configurations, which are commonly used in clinical practice, would be a cruciate configuration (shown) or a stacked mattress configuration.

Figure 26:
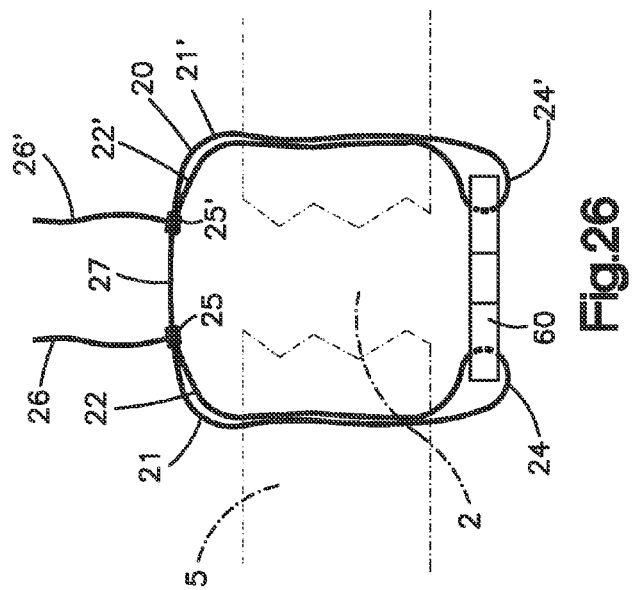
FIG. 26 illustrates an alternative tissue repair system and method including a mulit-loop suture in accordance with the present invention.

Additionally, or alternatively, the systems and methods described above may utilize two suture loops (each with its own sliding knot and free strand) on the same strand of suture. For example, referring to FIG. 26 a suture based tissue repair system and method is disclosed which includes a multi-loop suture 20 and a suture clasp 60. In FIG. 26 only two loops 21, 21' are illustrated but more than two loops may be possible. The loops 21, 21', 21", etc. may be pre-tied with one or more knots 25, 25', 25", etc. which, in various embodiments can include any type of sliding knot, ratcheting knot, or locking knot now or hereafter known in the art. In a preferred embodiment, the knots are a ratcheting and/or locking knot that prevents post-operative loosening of the repair construct. Each suture loop 21, 21', 21", etc. preferably includes a first loop end 22, 22', 22", etc., a second loop end 24, 24' 24", etc., and a free length of suture strand 26, 26', 26", etc. adjacent to and extending from the knot 25, 25', 25", etc. In this embodiment, the free suture strand 27 adjacent the knot 25 extends to the adjacent knot 25'. The clasp 60 in FIG. 26 may be any one of the clasps, or clips described or illustrated herein, or additional or alternative clasps or clips. The multi-loop suture may be utilized as described in the methods herein, and preferably the suture loops and the clasp or clip in combination work in series to close the tissue gap and reapproximate the tissue. While the multi-loop suture 20 may be supplied to the hospital, operating center or operating room with a pre-formed or pre-tied knot and multiple loops 21, 21', 21", etc., the suture 20 may also be configured in the operating room before or during the surgery to include loops 21, 21'; first loop ends 22, 22'; second loop ends 24, 24'; knots 25, 25' and free strands 26, 26'.

Referring to FIG. 24, an alternate system and method similar to that shown and described when referring to FIG. 4 is shown. The system and method of FIG. 24 includes the clasp 51 of FIG. 4 and further includes a plug 55 for occluding the annular defect, which is well suited for circumstances in which the annular defect is too large to allow adequate reapproximation using only the sutures and clasps described above. The plug 55 preferably is formed of a compliant biocompatible material, such as collagen, cellulose, hydrogels, etc., and may serve as a scaffold to facilitate healing. The plug 55 is connected to clasp construct 60, and the plug 55 can be attached to the clasp 60 via direct means, such as adhesive, or may be attached using connecting bands or sutures or any additional means. In use, the plug is positioned in the annulus defect and encircled by the suture loop and clasp. The plug/clasp assembly can be implanted and used as described in connection with FIGS. 4 and 5A-E, where the suture loop ends are connected to the clasp while outside of the disc space as shown in FIG. 24A and then the plug/clasp assembly is drawn into the annulus defect with the plug preferably remaining at least partially within the annulus opening as shown in FIG. 24B.

Alternatively, the plug can include a suture-locking mechanism that eliminates the need for a suture loop with a pre-tied knot. In such an embodiment, one strand of suture is passed through a full-thickness stitch encircling the annulus defect and the free strands of the suture are routed through the suture-locking mechanism within the defect or within the disc space. The suture-locking mechanism can be, for example, a locking dowel within an outer cylindrical sheath as described below in connection with FIG. 25. The suture-locking mechanism can optionally be surrounded by a biomaterial to provide a scaffold and fill the annulus defect. The suture-locking mechanism can optionally be located within the disc (i.e. not within the annulus defect).

Figure 25D:
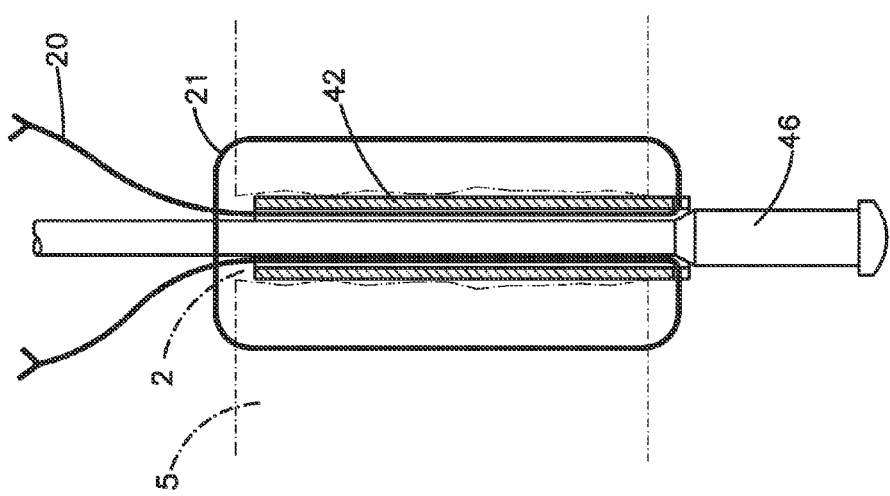
Figure 25C:
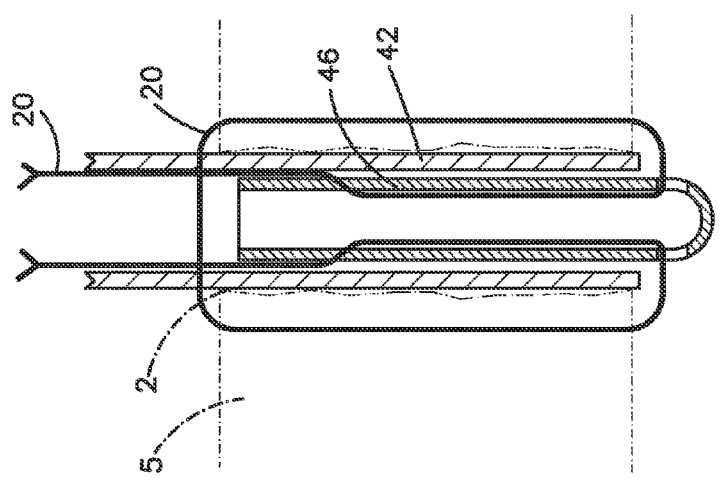

Referring to FIG. 25, an annulus repair system and method is provided that includes a suture 20, a locking anchor 85, and an inserter instrument 40 that further includes an inserter shaft 42 and a trigger-activated plunger 44. The locking anchor 85 further includes a locking sheath 46 and a locking dowel 48. The locking anchor may be pre-loaded onto the inserter instrument. Using a suture passer and retriever instrument similar to that previously described, a continuous strand of suture is passed through the annulus such that its free ends are retrieved through the defect, similar in configuration to FIG. 10, with the exception that a single strand of suture is passed, rather than a suture loop with a pre-tied sliding knot. The free ends of the suture are then threaded through the locking sheath of the locking anchor, which is loaded onto the inserter instrument. The locking anchor 85 and inserter instrument 40 are then passed into or through the annulus defect, the free strands are tensioned to reapproximate the annular defect, and the trigger-activated plunger 44 is advanced to allow the locking dowel 48 to engage the locking sheath 46, thereby locking the free strands of suture 20 within the locking anchor 85. The inserter tool 50 is then disengaged from the locking anchor 85, and the free strands of suture are cut.

It will be appreciated by those skilled in the art that changes could be made to the embodiments described above without departing from the broad inventive concept thereof. It is understood, therefore, that this invention is not limited to the particular embodiments disclosed, and features and structures may be used singularly or in combination, and it is intended to cover modifications within the spirit and scope of the present invention as defined by the appended claims.

We claim:

1. A system configured to approximate bodily tissue, the system comprising:
    a strand of suture having at least one loop, at least one knot that closes the at least one loop, and a free length of suture that extends from the at least one knot, the at least one loop defining a first closed loop end and a second closed loop end; and
    a clasp device having:
        first and second side surfaces that are spaced from one another along a first direction by a first dimension;
        first and second opposed end surfaces that extend between the first and second side surfaces, and that are spaced from one another along a second direction, perpendicular to the first direction;
        upper and lower surfaces that extend between the first and second side surfaces and between the first and second opposed end surfaces; and
        a central body portion having a free end that terminates at a third side surface, and having a pair of internal end surfaces that are spaced from one another along the second direction and that extend from the third side surface towards the second side surface, the second and third side surfaces facing away from one another and spaced from one another along the first direction by a second dimension that is no greater than the first dimension, the clasp device defining a first eyelet that extends from the upper surface to the lower surface and between the central body portion and the first end surface, a first slot open to both the first eyelet and the first side surface, a second eyelet that extends from the upper surface to the lower surface and between the central body portion and the second end surface, and a second slot open to both the second eyelet and the first side surface, the clasp device including, for each of the first and second eyelets, first and second interior surfaces that at least partially define the respective first and second eyelets, each second interior surface spaced between the second side surface and a respective one of the first interior surfaces along the first direction such that the central body portion extends from the third side surface past the second interior surfaces to the second side surface along the first direction, the clasp device defining an overall dimension from the first end surface to the second end surface along the second direction, and a maximum dimension from the second side surface to one of the second interior surfaces along the first direction, the maximum dimension being less than the overall dimension,
    wherein the clasp device is configured to join the first closed loop end and the second closed loop end by passing the first closed loop end through the first slot and into the first eyelet and the second closed loop end through the second slot and into the second eyelet such that when the free length of suture is pulled, the bodily tissue is approximated.

2. The system of claim 1 wherein the first eyelet and the second eyelet are configured such that the first closed loop end and the second closed loop end extend in opposite lateral directions from the clasp.

3. The system of claim 1 further comprising a suture passer and retriever instrument.

4. The system of claim 1, wherein the clasp device and strand of suture are configured and sized to repair a defect in an annulus of a spinal disc.

5. The system of claim 1, wherein the maximum dimension is less than a dimension from one of the second interior surfaces to the first side surface.

6. The system of claim 5, wherein the clasp device defines a second maximum dimension from the first side surface to one of the first interior surfaces, the second maximum dimension being less than the dimension from the one of the second interior surfaces to the first side surface.

7. The system of claim 1, wherein the central portion extends from the second side surface past the second interior surfaces to the third side surface along the first direction.

8. The system of claim 1, wherein the pair of end surfaces extend from the third side surface to the second interior surfaces.

9. A system configured to approximate a soft tissue defect, the system comprising:
    a strand of suture that defines at least one loop having two closed ends, the strand of suture including a sliding, locking, or ratcheting knot, and a free end that extends from the knot; and
    a clasp device having:
        first and second side surfaces spaced from one another along a first direction;
        first and second opposed ends that extend between the first and second side surfaces;
        upper and lower surfaces that extend between the first and second side surfaces and between the first and second opposed ends;
        a central body portion having a free end that terminates at a third side surface that faces the first direction, and a pair of end surfaces that are spaced from one another along a second direction, perpendicular to the first direction, the pair of end surfaces extending from the third side surface towards the second side surface along the first direction, and the central body portion extending from the second side surface to the third side surface along the first direction without extending beyond the first side surface such that the central body portion has a length from the second side surface to the third side surface along the first direction,
        a first arm that extends from the central body portion toward the first end along the second direction; and
        a second arm that extends from the central body portion toward the second end in a direction that is away from the first arm and opposite the second direction,
    wherein each arm at least partially defines an opening that extends from the upper surface to the lower surface, each opening is open to the first side surface, the second side surface is devoid of openings at the upper surface, and the length of the central body portion is greater than a greatest dimension of each of the openings along the first direction, wherein the clasp device is configured to secure the two closed ends of the loop by routing each closed end into a different one of the openings, and wherein the strand of suture and clasp device are configured in combination to surround the soft tissue defect and at least partially approximate the soft tissue defect.

10. The system of claim 9 wherein the strand of suture and clasp device are configured to be in series so as to form a second loop, different from the first loop, the second loop surrounding the soft tissue defect.

11. The system of claim 9 further comprising a needle configured to releasably attach to the strand of suture and configured to pass the strand of suture through the soft tissue.

12. The system of claim 11 further comprising a suture passer and retriever instrument, the suture passer and retriever instrument is configured to cooperate with the needle.

13. The system of claim 12 wherein the suture passer and retriever instrument comprises a boom arm configured to capture the strand of suture.

14. The system of claim 13 wherein the suture passer and retriever instrument is releasably coupleable to the clasp device.

15. The system of claim 12 wherein the suture passer and retriever instrument comprises a wire loop configured to capture the strand of suture.

16. The system of claim 12 wherein the suture passer and retriever instrument further comprises two needles, each needle connectable to an end of the strand of suture and being independently moveable, the clasp device being releasably connectable to the suture passer and retriever instrument, the clasp device having an opening for receiving the strand of suture.

17. The system of claim 9 further comprising a plug member configured to fill and seal the soft tissue defect.

18. The system of claim 9, wherein each arm has an interior surface that at least partially defines a respective one of the openings, and an outer surface opposite the interior surface, and wherein the central body portion extends from the interior surfaces to the third side surface along the first direction.

19. The system of claim 18, wherein the pair of end surfaces extends from the interior surfaces to the third side surface.

* * * * *